(12) United States Patent  (10) Patent No.: US 9,417,198 B2
Green et al.  (45) Date of Patent: Aug. 16, 2016

(54) DETECTION OF CARBON NANOTUBES BY MICROWAVE-INDUCED HEATING

(71) Applicant: Texas Tech University System, Lubbock, TX (US)

(72) Inventors: Micah J. Green, Lubbock, TX (US); Fahmida Irin, Lubbock, TX (US); Jaclyn Cañas, Lubbock, TX (US); Mohammad Saed, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 606 days.

(21) Appl. No.: 13/780,624

(22) Filed: Feb. 28, 2013

(65) Prior Publication Data

US 2013/0259085 A1  Oct. 3, 2013

Related U.S. Application Data

(60) Provisional application No. 61/604,369, filed on Feb. 28, 2012.

(51) Int. Cl.
  *G01N 25/00* (2006.01)
  *G01K 7/00* (2006.01)
  *G01J 5/00* (2006.01)
  *G01N 22/00* (2006.01)

(52) U.S. Cl.
  CPC ............... *G01N 25/00* (2013.01); *G01N 22/00* (2013.01); *G01N 25/005* (2013.01)

(58) Field of Classification Search
  USPC ....................................... 374/45, 179, 57, 122
  See application file for complete search history.

(56) References Cited

U.S. PATENT DOCUMENTS

| | | | | |
|---|---|---|---|---|
| 8,080,199 | B2 * | 12/2011 | Tour | B82Y 30/00 204/157.43 |
| 2008/0227168 | A1 | 9/2008 | Kmecko et al. | |
| 2009/0255799 | A1 * | 10/2009 | Harutyunyan | B01J 19/126 204/157.43 |
| 2010/0296996 | A1 * | 11/2010 | Ohta | B82Y 30/00 423/447.7 |
| 2011/0024333 | A1 * | 2/2011 | Han | B82Y 30/00 209/7 |
| 2011/0171110 | A1 * | 7/2011 | Viswanathan | B82Y 30/00 423/447.2 |
| 2013/0293429 | A1 * | 11/2013 | Keller | H01Q 1/00 343/720 |

OTHER PUBLICATIONS

Aitken RJ, et al., "Manufacture and use of nanomaterials: current status in the UK and global trends." Occup Med 2006;56:300-6.
Alloy MM, et al., "Effects of suspended multi-walled carbon nanotubes on daphnid growth and reproduction." Ecotoxicol Environ Saf 2011;74:1839-43.
Amiran J, et al., "High quality dispersions of functionalized single walled nanotubes at high concentration." J Phys Chem C 2008;112:3519-24.

(Continued)

*Primary Examiner* — Mirellys Jagan
(74) *Attorney, Agent, or Firm* — Chainey P. Singleton; Edwin S. Flores; Chalker Flores, LLP

(57) ABSTRACT

The present invention includes a method, systems and devices for the detection of carbon nanotubes in biological samples by providing a sample suspected of having one or more carbon nanotubes; irradiating the sample with a microwave radiation, wherein the carbon nanotubes absorb the microwave radiation; and detecting and measuring the one or more thermal emissions from the carbon nanotubes.

20 Claims, 8 Drawing Sheets

(56) References Cited

OTHER PUBLICATIONS

Brunetti FG, et al., "Microwave-Induced Multiple Functionalization Of Carbon Nanotubes. Journal of the American Chemical Society." Jun. 2008;130(25):8094-100.

Brunetti FG, et al., "Reversible Microwave-Assisted Cycloaddition Of Aziridines To Carbon Nanotubes." Journal of the American Chemical Society. Nov. 2007;129(47):14580-+.

Cañas JE, et al., "Effects of functionalized and nonfunctionalized single-walled carbon nanotubes on root elongation of select crop species." Environ Toxicol Chem 2008;27:1922-31.

Cerqueira B, et al., "Time of flight secondary ion mass spectrometry and high-resolution transmission electron microscopy/energy dispersive spectroscopy: a preliminary study of the distribution of Cu2+ and Cu2+/Pb2+ on a Bt horizon surfaces." J Hazard Mater 2011:422-31.

Cerqueira B, et al., "Effects of vegetation on chemical and mineralogical characteristics of soils developed on a decantation bank from a copper mine." Sci Total Environ 2012;421-422:220-9.

Cheng J, et al., "Effect of carbon nanotubes on developing zebrafish (Danio rerio) embryos." Environ Toxicol Chem 2007;26:708-16.

Chowdhury SR, Chen Y, Wang Y, Mitra S. Microwave-Induced Rapid Nanocomposite Synthesis Using Dispersed Single-Wall Carbon Nanotubes As The Nuclei. Journal of Materials Science. Mar. 2009;44(5):1245-50.

Green MJ. "Analysis and measurement of carbon nanotube dispersions: nanodispersion versus macrodispersion." Polym Int 2010;59:1319-22.

Higginbotham AL, et al., "Carbon Nanotube Composite Curing Through Absorption of Microwave Radiation." Composites Science and Technology. Dec. 2008;68(15-16):3087-92.

Iijima S. "Helical Microtubules of Graphitic Carbon." Nature. Nov. 7, 1991;354(6348):56-8.

Imholt TJ, et al., "Nanotubes in Microwave Fields: Light Emission, Intense Heat, Outgassing, And Reconstruction." Chemistry of Materials. Oct. 2003;15(21):3969-70.

Irin F, et al., "Detection of carbon nanotubes in biological samples through microwave-induced heating." Carbon 2012;50:4441-9.

Kang S, et al., "Antibacterial Effects of Carbon Nanotubes: Size Does Matter" Langmuir. Jul. 1, 2008;24(13):6409-13.

Khodakovskaya M, et al., "Carbon Nanotubes Are Able to Penetrate Plant Seed Coat and Dramatically Affect Seed Germination and Plant Growth." Acs Nano. Oct. 2009;3(10):3221-7.

Khodakovskaya MV, et al., "Complex Genetic, Photothermal, and Photoacoustic Analysis of Nanoparticle-Plant Interactions." Proceedings of the National Academy of Sciences of the United States of America. Jan. 18, 2011;108 (3):1028-33.

Ko FH, et al., "Purification Of Multi-Walled Carbon Nanotubes Through Microwave Heating Of Nitric Acid In A Closed Vessel." Carbon. 2005;43(4):727-33.

Lam, C-w, et al., "A review of carbon nanotube toxicity and assessment of potential occupational and environmental health risks." Crit Rev Toxicol 2006;36:189-217.

Leeuw TK, et al., "Single-walled carbon nanotubes in the intact organism: near-IR imaging and biocompatibility studies in drosophila." Nano Lett 2007;7:2650.

Li Y-H, et al., "Dielectric Constants Of Single-Wall Carbon Nanotubes At Various Frequencies." Journal of Nanoscience and Nanotechnology. Sep. 2007;7(9):3185-8.

Liu Q, et al., "Carbon Nanotubes As Molecular Transporters for Walled Plant Cells." Nano Letters. Mar. 2009;9.(3):1007-10.

Liu Z, et al., "Circulation and long-term fate of functionalized, biocompatible single-walled carbon nanotubes in mice probed by Raman spectroscopy." Proc Natl Acad Sci U S A 2008;105:1410-5.

Masciangioli T, et al., "Environmental Technologies At The Nanoscale. Environmental Science & Technology." Mar. 1, 2003;37(5):102A-8A.

Mashal A, et al., "Toward Carbon-Nanotube-Based Theranostic Agents for Microwave Detection And Treatment Of Breast Cancer: Enhanced Dielectric And Heating Response Of Tissue-Mimicking Materials." Ieee Transactions on Biomedical Engineering. 2010;57(8)1831-4.

Navarro E, et al. "Environmental Behavior And Ecotoxicity Of Engineered Nanoparticles To Algae, Plants, And Fungi." Ecotoxicology. Jul. 2008;17(5):372-86.

Oliveira MLS, et al., "Mineralogy and leaching characteristics of beneficiated coal products from Santa Catarina, Brazil." Int J Coal Geol 2012a;94:314-25.

Petersen EJ, et al., "Biological uptake and depuration of carbon nanotubes by *Daphnia magna*." Environ Sci Technol 2009a;43:2969-75.

Petersen EJ, et al., "Bioaccumulation of radio-labeled carbon nanotubes by *Eisenia foetida*." Environ Sci Technol 2008;42:3090.

Petersen EJ, et al., "Influence of carbon nanotubes on pyrene bioaccumulation from contaminated soils by earthworms." Environ Sci Technol 2009b;43:4181-7.

Petersen EJ, et al., "Effects of polyethyleneimine-mediated functionalization of multi-walled carbon nanotubes on earthworm bioaccumulation and sorption by soils" Environ Sci Technol 2011;45: 3718-24.

Plata DL, et al., "Thermogravimetry—mass spectrometry for carbon nanotube detection in complex mixtures." Environ Sci Technol 2012.

Quispe D, et al., "Changes in mobility of hazardous elements during coal combustion in Santa Catarina power plant (Brazil)." Fuel 2012;94:495-503.

Ribeiro J, et al., "Identification of nanominerals and nanoparticles in burning coal waste piles from Portugal." Sci Total Environ 2010;408:6032-604.

Shieh YT, et al., "Effects of pH on electrocatalytic activity of functionalized carbon nanotubes." Colloid Polym Sci 2012;290:1-9.

Shim HC, et al., "Enhancement of Adhesion Between Carbon Nanotubes and Polymer Substrates Using Microwave Irradiation." Scripta Materialia. Jul. 2009;61(1):32-5.

Shim HC, et al., "Preferential elimination of metallic single-walled carbon nanotubes using microwave irradiation." Nanotechnology 2009;20.

Silva LFO, et al., "The occurrence of hazardous volatile elements and nanoparticles in Bulgarian coal fly ashes and the effect on human health exposure." Sci Total Environ 2012c;416:513-26.

Silva LFO, et al., "Applied investigation on the interaction of hazardous elements binding on ultrafine and nanoparticles in Chinese anthracite-derived fly ash." Sci Total Environ 2012d;419:250-64.

Silva LFO, et al., "Nanominerals and ultrafine particles in sublimates from the Ruth Mullins coal fire, Perry County, Eastern Kentucky, USA." Int J Coal Geol 2011;85:237-45.

Silva LFO, et al., "Geochemistry of carbon nanotube assemblages in coal fire soot, Ruth Mullins fire, Perry County, Kentucky." Int J Coal Geol 2012a;94:206-13.

Silva LFO, et al., "Multianalytical approaches to the characterisation of minerals associated with coals and the diagnosis of their potential risk by using combined instrumental microspectroscopic techniques and thermodynamic speciation." Fuel 2012b;94:52-63.

Sobek A, et al., "Testing the resistance of single- and multi-walled carbon nanotubes to chemothermal oxidation used to isolate soots from environmental samples." Environ Pollut 2009;157: 1065-71.

Vazquez E, et al., "Carbon Nanotubes and Microwaves: Interactions, Responses, and Applications." Acs Nano. Dec. 2009;3(12):3819-24.

Wang L, et al., "Carbon Nanotube Composites With High Dielectric Constant At Low Percolation Threshold." Applied Physics Letters. Jul. 2005;87(4).

Yang K, et al., "Adsorption of Polycyclic Aromatic Hydrocarbons by Carbon Nanomaterials." Environmental Science & Technology. Mar. 15, 2006;40(6):1855-61.

Yang M, et al., "Study Of The Biouptake Of Labeled Single-Walled Carbon Nanotubes Using Fluorescence-Based Method." Environmental Chemistry Letters. Jun. 2011;9(2):235-41.

Zhao X, et al., "Recent progress and perspectives on the toxicity of carbon nanotubes at organism, organ, cell, and biomacromolecule levels." Environ Int 2012;40:244-55.

\* cited by examiner

DETECTION OF CARBON NANOTUBES BY MICROWAVE-INDUCED HEATING

CROSS-REFERENCE TO RELATED APPLICATIONS

This application claims priority based on U.S. Provisional Application No. 61/604,369, filed Feb. 28, 2012. The contents of which is incorporated by reference in its entirety.

STATEMENT OF FEDERALLY FUNDED RESEARCH

This invention was made with U.S. government support under Grant No. CBET1133250 awarded by the NSF. The government has certain rights in the invention.

TECHNICAL FIELD OF THE INVENTION

The present invention relates in general to the field of detection of carbon nanotubes (CNT), specifically to compositions of matter and methods for the quantitative detection of CNT in biological samples.

INCORPORATION-BY-REFERENCE OF MATERIALS FILED ON COMPACT DISC

None.

BACKGROUND OF THE INVENTION

Without limiting the scope of the invention, its background is described in connection with methods and devices for the detection of CNT's.

Carbon nanotubes are among the most widely used carbon-based nanomaterials. Carbon nanotubes (CNTs) are $sp^2$-hybridized carbon arranged in a cylindrical nanostructure, and CNTs attracted much attention after Iijima's remarkable paper on carbon nanotubes in 1991. Since then, CNTs have been studied and applied intensively in various fields because of their fascinating electrical, mechanical, and thermal properties.

One area of potential CNT use is in the area of agricultural production, such as smart delivery systems, nanoemulsions, nanosensors, and nanocatalysts for pesticides and other chemicals. Currently, thousands of chemicals are used for agricultural production throughout the United States. Many compounds have a high adsorption affinity for organic carbon and allow CNTs to act as a vehicle for delivery of agricultural chemicals to sites of toxic action or certain surfaces in pest species. In addition, nanomaterials may be used as modifiers of chemical behavior in the environment and for contaminant remediation that can reduce risk to non-target organisms. Common methods of detecting trace amounts of CNT, i.e. electron microscopy, Raman spectroscopy, florescence, etc., have practical difficulties that limit effectiveness and limit the detection.

Prior to this discovery, the majority of art patents and publications describe the use of microwaves for the creation and purification of CNT's. Most prior art methods use electrical current as a thermal generator and detail the unusually high thermal conductivity in CNTs but do not detail microwave application as a method to induce thermal conductivity as a detection method. For example, U.S. Pat. No. 8,080,199, entitled, "Interaction of microwaves with carbon nanotubes to facilitate modification," discloses crosslinking of carbon nanotubes to each other using microwave radiation, articles of manufacture produced by such methods, compositions produced by such methods, and applications for such compositions and articles of manufacture.

U.S. Patent Application Publication No. 20080227168 entitled, "Methods and Materials for Extra and Intracellular Delivery of Carbon Nanotubes," discloses compositions and methods to deliver carbon nanostructures that include agents for delivery to cells, wherein the carbon nanostructure and the agent are made soluble by coating the carbon nanostructure with one or more polymers, e.g., low band gap conductive polymers.

SUMMARY OF THE INVENTION

One embodiment of the present invention provides a novel use of microwave exposure to determine the existence and amount of carbon nanotubes (CNTs) in biological samples. Furthermore, the present invention provides a method for detecting CNTs at concentrations of about 0.04, 0.05, 0.06, 0.07, 0.075 µg or greater, in contrast to current techniques that allow detection concentrations of about 30 µg.

One embodiment of the present invention provides methods, devices and systems for quantitative detection of CNT in biological samples by utilizing the microwave assisted heating of CNT. CNT have an unusual physical property of evolving extreme amounts of heat when exposed to microwaves and the response is much more intense than conventional materials. One embodiment of the present invention provides exposing CNT loaded samples to microwaves and quantitatively measuring the CNT concentration in that sample.

The present invention provides a method of detecting carbon nanotubes in a sample by providing a sample suspected of having one or more carbon nanotubes; irradiating the sample with one or more microwave radiations; adsorbing the one or more microwave radiations by the one or more carbon nanotubes absorb; generating one or more thermal emissions from the one or more carbon nanotubes; and detecting the one or more thermal emissions from the one or more carbon nanotubes in the sample.

The one or more microwave radiations that may include a single microwave radiation or may include a first microwave radiation and a second microwave radiation. In other embodiments, the one or more microwave radiations may include a third, fourth, fifth, or more microwave radiations and may be at the same, different or reoccurring frequencies, duration, intensities. For example, the first microwave radiation may be 30 W at 2.45 GHz frequency and the second microwave radiation may be 50 W at 2.45 GHz frequency. Generally, the one or more microwave radiations may have a frequency between 300 GHz-300 MHz or 1 mm-1 meter. For example, the microwave radiation may have a frequency of 1.1 GHZ, 1.15 GHZ, 1.2 GHZ, 1.25 GHZ, 1.3 GHZ, 1.35 GHZ, 1.4 GHZ, 1.45 GHZ, 1.5 GHZ, 1.55 GHZ, 1.6 GHZ, 1.65 GHZ, 1.7 GHZ, 1.75 GHZ, 1.8 GHZ, 1.85 GHZ, 1.9 GHZ, 1.95 GHZ, 2.00 GHz, 2.1 GHZ, 2.15 GHZ, 2.2 GHZ, 2.25 GHZ, 2.3 GHZ, 2.35 GHZ, 2.4 GHZ, 2.45 GHZ, 2.5 GHZ, 2.55 GHZ, 2.6 GHZ, 2.65 GHZ, 2.7 GHZ, 2.75 GHZ, 2.8 GHZ, 2.85 GHZ, 2.9 GHZ, 2.95 GHZ, 3.00 GHz, 3.1 GHZ, 3.15 GHZ, 3.2 GHZ, 3.25 GHZ, 3.3 GHZ, 3.35 GHZ, 3.4 GHZ, 3.45 GHZ, 3.5 GHZ, 3.55 GHZ, 3.6 GHZ, 3.65 GHZ, 3.7 GHZ, 3.75 GHZ, 3.8 GHZ, 3.85 GHZ, 3.9 GHZ, 3.95 GHZ, 4.00 GHz. The one or more microwave radiations may be between 0-140 W, 5-130 W, 5-120 W, 5-110 W, 5-100 W, 10-90 W, 10-80 W, 20-70 W, 30-60 W, 30-50 W, 40-60 W, 40-50 W or incrimental variations thereof and the one or more microwave radiations may have a resolution of 0.1 W, 0.2 W, 0.3 W, 0.4 W, 0.5 W, 0.6 W, 0.7 W, 0.8 W, 0.9 W, 1 W, 1.1 W, 1.2 W, 1.3 W, 1.4 W, 1.5 W or more. In addition some embodiments include the step of flowing a continuous flow of nitrogen directly onto the surface of the sample to prevent ignition.

The present invention provides contacting a thermocouple probe with the sample to measure a temperature change resulting from the one or more thermal emissions. The thermocouple probe may be a k-type beaded wire stainless steel thermocouple. The one or more carbon nanotubes detection may have a detection limit of between 0.04-30 µg and specifically the detection may be about 0.04, 0.05, 0.06, 0.07, 0.075 µg or greater.

The present invention provides the step of correlating the one or more thermal emissions to the concentration of the one or more carbon nanotubes. The method also includes comparing the one or more thermal emissions to a carbon nanotube temperature/concentration of standard.

The sample may be a biological sample or an environmental sample. The samples may include a plant tissue, an animal tissue, a human tissue, a plant cell, an animal cell, a human cell, a cancer cell, and so forth. Specific examples include plant roots or earthworms.

The one or more carbon nanotubes may be single walled carbon nanotubes, multi-walled nanotubes, or a combination thereof. In some embodiments, carbon nanotubes may actually be carbon nanoparticles. The one or more single walled carbon nanotubes may have a diameter of between 0.1-2.0 nm, 0.2-1.9 nm, 0.3-1.8 nm, 0.4-1.8 nm, 0.5-1.7 nm, 0.6-1.6 nm, 0.7-1.5 nm, 0.7-1.3 nm or an incremental variation thereof and a diameter of 10-70 nm, 15-65 nm, 20-60 nm, 25-55 nm, 30-50 nm, 35-45 nm or an incremental variation thereof and a length of between 5-25 µm, 7-22 µm, 10-20 µm, or more than 25 µm.

Another embodiment includes a device and system for the detection of carbon nanotubes including a sample chamber to receive a sample comprising one or more carbon nanotubes; a microwave radiation source positioned to irradiate the sample chamber; a thermal detector to detect one or more thermal emissions from the sample; and an output mechanism connected to the thermal detector to transmit the one or more thermal emissions. The device and system further include a source of continuous flow of a nitrogen gas to the sample chamber to prevent ignition. The microwave radiation source irradiates the sample chamber at different wavelengths, times, angles or combination thereof and a comparison means to compare the one or more thermal emissions to a standard, wherein the temperature change is related to the concentration of CNTs.

The present invention provides a device for the detection of carbon nanotubes including a sample chamber to receive a sample having one or more carbon nanotubes; one or more microwave radiation sources positioned to irradiate the sample chamber; a thermal detector in contact with the sample chamber to detect one or more thermal emissions from the sample; and an output mechanism connected to the thermal detector to transmit the one or more thermal emissions.

The microwave radiation source may irradiate the sample chamber at different wavelengths, times, angles or combination thereof. The one or more microwave radiation sources may include a first microwave radiation source at a first angle and a second microwave radiation source at a second angle. The one or more microwave radiation sources may also include a first microwave radiation source at a first frequency, duration, and/or intensity and a second microwave radiation source at a second frequency, duration, and/or intensity. The microwave radiation source may have a frequency of 1.1 GHZ, 1.15 GHZ, 1.2 GHZ, 1.25 GHZ, 1.3 GHZ, 1.35 GHZ, 1.4 GHZ, 1.45 GHZ, 1.5 GHZ, 1.55 GHZ, 1.6 GHZ, 1.65 GHZ, 1.7 GHZ, 1.75 GHZ, 1.8 GHZ, 1.85 GHZ, 1.9 GHZ, 1.95 GHZ, 2.00 GHz, 2.1 GHZ, 2.15 GHZ, 2.2 GHZ, 2.25 GHZ, 2.3 GHZ, 2.35 GHZ, 2.4 GHZ, 2.45 GHZ, 2.5 GHZ, 2.55 GHZ, 2.6 GHZ, 2.65 GHZ, 2.7 GHZ, 2.75 GHZ, 2.8 GHZ, 2.85 GHZ, 2.9 GHZ, 2.95 GHZ, 3.00 GHz, 3.1 GHZ, 3.15 GHZ, 3.2 GHZ, 3.25 GHZ, 3.3 GHZ, 3.35 GHZ, 3.4 GHZ, 3.45 GHZ, 3.5 GHZ, 3.55 GHZ, 3.6 GHZ, 3.65 GHZ, 3.7 GHZ, 3.75 GHZ, 3.8 GHZ, 3.85 GHZ, 3.9 GHZ, 3.95 GHZ, 4.00 GHz. The microwave radiation source may have a frequency of 2.45 GHz. The one or more microwave radiations may include a first microwave radiation and a second microwave radiation. In addition, the one or more microwave radiations may include a third, fourth, fifth, or more microwave radiations and may be at the same, different or reoccurring frequencies, duration, intensities. For example, the first microwave radiation may be 30 W at 2.45 GHz frequency and the second microwave radiation may be 50 W at 2.45 GHz frequency. Generally, the one or more microwave radiations may have a frequency between 300 GHz-300 MHz or 1 mm-1 meter. The one or more microwave radiations may be between 0-140 W, 5-130 W, 5-120 W, 5-110 W, 5-100 W, 10-90 W, 10-80 W, 20-70 W, 30-60 W, 30-50 W, 40-60 W, 40-50 W or incrimental variations thereof and the one or more microwave radiations may have a resolution of 0.1 W, 0.2 W, 0.3 W, 0.4 W, 0.5 W, 0.6 W, 0.7 W, 0.8 W, 0.9 W, 1 W, 1.1 W, 1.2 W, 1.3 W, 1.4 W, 1.5 W or more. The thermal detector may be a thermocouple probe. The device may further include a comparison means to compare the one or more thermal emissions to a thermal emissions standard that correlates a temperature change to a carbon nanotube concentration. The device may further include a cooling source in communication with the sample chamber to prevent ignition, wherein the cooling source is a continuous flow of a nitrogen gas. The thermal detector may be a k-type beaded wire stainless steel thermocouple. The device may further include a microwave WR-284 waveguide in contact with the microwave radiation source.

One embodiment of the present invention includes methods and apparatuses used to detect and quantify MWNTs in organisms by microwave induced heating. The present invention provides a new procedure for quantifying multi-walled carbon nanotubes (MWNTs) in earthworms (*Eisenia fetida*) based on freeze drying and microwave-induced heating. This technique can be used to quantify MWNTs in a variety of sample types (e.g., plants, earthworms, human blood, and biological samples).

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
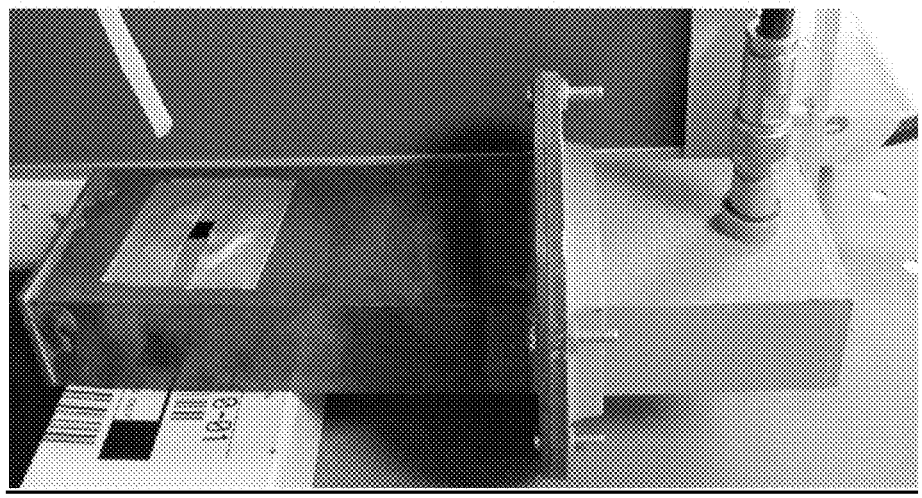
FIG. 1 is an image of the WR-284 waveguide used in one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Carbon nanotubes are among the most widely used carbon-based nanomaterials. The present invention provides devices, systems and methods of making and using the same to benefit agricultural production, such as smart delivery systems for pesticides and other chemicals. In addition, the wide ranging applications of CNT have increasing opportunities to pervade the environment, including uptake into the roots of agricultural crops from CNT in agricultural pesticides and other products that might deposit CNT in soil. However, until the present invention, the common methods of detecting trace amounts of CNT, i.e. electron microscopy, Raman spectroscopy, florescence etc. have practical difficulties that limit effectiveness and limit the detection. In addition, the present invention provides for a reliable and affordable analytical method and device to determine CNTs in biotic and abiotic samples, since studies regarding CNT toxicity and fate of CNT in various aquatic and terrestrial organisms and environments are heavily dependent upon determination of CNT concentrations, which has until the present invention been limited.

The present invention provides methods and devices for the quantitative detection of CNT in agricultural, biological and other samples which is not possible to develop based on common analytical methods such as electron microscopy and Raman spectroscopy with a threshold limit of detectable CNT concentration (<0.1 µg); this value is considerably lower than the probable detectable limit of electron microscopy or Raman spectroscopy.

One embodiment of the present invention provides novel techniques and devices for the quantitative detection of carbon nanotubes (CNTs) in biological samples by utilizing the thermal response of CNTs under microwave irradiation. The rapid heating of CNTs by microwave absorption is employed to quantify CNT absorption in samples with excellent sensitivity. One example includes the injection of alfalfa (*Medicago sativa*) roots with a known quantity of CNTs (single walled and multi-walled) and expose the samples to a microwave field (30-50 W) to generate standard temperature-CNT concentration relationships to accurately determine CNT absorption by alfalfa plant roots grown in CNT-laden soil. The threshold for detectable CNT concentration is much lower (<0.1 µg) than common analytical methods such as electron microscopy and Raman spectroscopy. Considering the lack of effective detection methods for CNT uptake in plants, the present invention is not only unique but also practical, as it addresses a major problem in the field of nanomaterial characterization and nanotoxicology risk assessment.

Carbon nanotubes (CNTs) are $sp^2$-hybridized carbon arranged in a cylindrical nanostructure and have attracted much attention after Iijima's remarkable paper on carbon nanotubes in 1991 [1]. Since then, CNTs have been studied and applied intensively in various fields because of their fascinating electrical, mechanical, and thermal properties [2]. One area of potential CNT use is innovative technology in the area of agricultural production, such as smart delivery systems, nanoemulsions, nanosensors, and nanocatalysts for pesticides and other chemicals. Currently, thousands of chemicals are used for agricultural production throughout the United States. Many compounds have a high adsorption affinity for organic carbon and allow CNTs to act as a vehicle for delivery of agricultural chemicals to sites of toxic action or certain surfaces in pest species. In addition, nanomaterials may be used as modifiers of chemical behavior in the environment [3] and for contaminant remediation [4] that can reduce risk to non-target organisms. CNTs of the present invention can also be used for nutrient, drug, agrochemical and biological delivery to specific cells, and the controlled release of these agents.

Many plant studies of CNTs are focused on the phytotoxicity (effects on germination, root elongation, plant growth, etc.) of these nanomaterials to various plant species. These studies demonstrate that nanotubes might alter essential biochemical processes necessary for plant growth and survival [6-8]. Given the ability of CNTs to cross plant cell walls and membranes, and the potential use of CNTs in agriculture, it is evident that reliable methods are needed to quantify CNTs in plants and other biological samples in a soil environment [9]. However, existing analytical methods are limited in their usefulness in this area. The most common techniques used for the detection and characterization of CNTs in such samples are scanning electron microscopy (SEM), transmission electron microscopy (TEM), and Raman spectroscopy. SEM and TEM can be used to image CNTs on plant surfaces or cross sections and compared against control samples. Raman spectroscopy probes vibrational modes in CNT bonds and can be used to detect the presence of CNTs on a surface. However, these techniques have serious limitations in detecting trace quantities of CNTs within a sample.

For instance, Khodakovskaya et al. used Raman spectroscopy and TEM on tomato seeds, roots, stem and leaves in order to detect CNT uptake [7]. A very small G (Graphite) peak was observed in the magnified Raman signal, which indicates the presence of CNTs inside a longitudinally cut sample of germinated tomato seed; however, it did not display any signal for CNTs in the sections (roots, stem and leaves) of the tomato seedlings. The authors identified CNTs in TEM images, but such image analysis can be problematic and subjective. (A follow-up report from the same group indicated that photothermal and photoacoustic analysis could be used to detect CNTs injected directly into a plant leaf [10].) Similarly, Cañas et al. reported the adsorption of nanotubes by the plant root as shown by SEM images of the root surface, but no CNTs inside the plant root could be detected [6]. Unfortunately, the absence of CNTs in electron microscopy (EM) images or Raman spectra can act as a false negative. Also, near-infrared fluorescence has been used to detect the presence of CNTs in macroscopic Drosophila flies whose food contained 10 ppm single walled carbon nanotubes (SWCNTs) [11]. Yang et al. utilized a similar technique to detect dye-labeled SWCNTs in worms [12]. However, this technique has limitations to use only in case of well dispersed SWCNTs as SWCNTs do not fluoresce when they are bundled and multi-walled carbon nanotubes (MWCNT) do not fluoresce at all. Moreover, it typically requires higher concentrations than the trace quantities of interest in the case of CNTs absorbed by plants. Raman spectroscopy is severely limited in its ability to detect trace quantities of CNTs inside a macroscopic sample. Similarly, SEM and TEM imaging can only be successful when CNTs are visible on exterior surfaces or the surfaces of cross sections. Furthermore, all of these techniques are prone to false negatives, i.e., a lack of detection can never guarantee the absence of CNTs. Finally, we note that quantitative measures of CNT concentration are difficult to establish based on those techniques.

Therefore, it is necessary to develop reliable methods to detect and quantify the presence of CNTs in biological samples. CNTs do have a peculiar physical property that might be leveraged to address this challenge and enable quantitative detection of CNTs. Due to strong absorption of microwaves, CNTs are known to evolve extreme amounts of heat when exposed to microwaves; this response is much more intense than conventional materials. This absorption also produces dramatic light emission, outgassing, and even CNT "welding" and cross-linking [13]. CNTs can be heated selectively under microwave irradiation [14] to a temperature of around 2000° C. [13, 15]. So far, this unique property of CNTs caused by the interaction with microwave irradiation has never been used to detect CNTs in plant samples and has never been utilized in any environmental application. Prior applications of microwaves to CNTs include the purification and separation of different types of CNTs [16, 17], processing of CNT-polymer composites [14, 18], functionalization of CNTs by the Bingel Reaction [19-21], CNT-ceramic composite curing [22], and determination of CNT dielectric properties [15, 23]. Another application of CNT-microwave heating is selective detection and demolition of cancer cells [24].

The exposure of root samples to microwaves can quantitatively measure the CNT concentration in that sample; the temperature profiles and morphology show the signatures of microwave-induced CNT heating. Thus, characterization methods based on microwave exposure address this critical scientific challenge of CNT detection and characterization in biological samples. The microwave-induced heating not only detects the presence of CNTs but also quantitatively measure concentration.

Single walled carbon nanotubes (SWCNT) were purchased from Aldrich Chemistry. The SWCNT has a purity >75% and diameter of 0.7-1.3 nm. Multi-walled nanotubes (MWCNT) of length 10-20 μm and diameter of 30-50 nm (purity >95 wt % and ash content <1.5 wt %) were purchased from Cheap tubes. Sodium dodecyl benzene sulfonate (SDBS) of $M_w$: 348.5 were obtained from Sigma Aldrich. All of these were used as received without any further purification.

FIG. 1 is an image of the WR-284 waveguide used in one embodiment of the present invention. This waveguide is designed for 2.45 GHz frequency microwaves. It is connected to the microwave generator with a co-axial cable. The waveguide is made of copper and the dimensions are 16 cm×4 cm. The glass sample holder is placed inside the hole drilled about 4 cm away from the closed end of the waveguide. A variable power microwave generator was purchased from Opthos Instruments Inc (model number: MPG 4 RF, LAB-909) shown in FIG. 1. The generator measures incident and reflected microwave powers (0-120 W) with a resolution of 1 W. It has built-in protection to handle total reflected power. The operating frequency of the generator is 2.45 GHz. A rectangular WR-284 waveguide which is able to guide 2.45 GHz frequency was designed and built for the present invention and is capable of measuring both applied and reflected power (0-120 W). The temperature of the sample was measured by a k-type beaded wire stainless steel thermocouple from Omega (Model SC-GG-K-30-36, ungrounded, 0.032" diameter). The thermocouple was connected to a digital multimeter (Omega model HHM290) which is able to read the temperature in the range of −200° C. to 1372° C.

Preparation of CNT dispersion. Stable aqueous dispersions of CNTs (SWCNT or MWCNT) were prepared using SDBS as a stabilizer [25]. 2% w/v SDBS were completely dissolved in water by magnetic stirring and 0.2 mg/mL CNTs were added to this solution. This mixture was then tip sonicated for 1 hour at an output power of 7 W (Misonix sonicator, XL 2000) and centrifuged (Centrific Centrifuge 225, Fischer Scientific) for 4 hours at a speed of ~5000 rpm. After centrifugation the supernatant was collected and the absorbance was measured by Shimadzu UV-vis spectrophotometer 2550 at wavelengths of 200 nm to 800 nm. Concentration of the dispersion was calculated from the absorbance (at 660 nm) using the Lambert-Beer law. The extinction co-efficient was taken as 3389 mL $mg^{-1}$ $m^{-1}$ [26].

Figure 2:
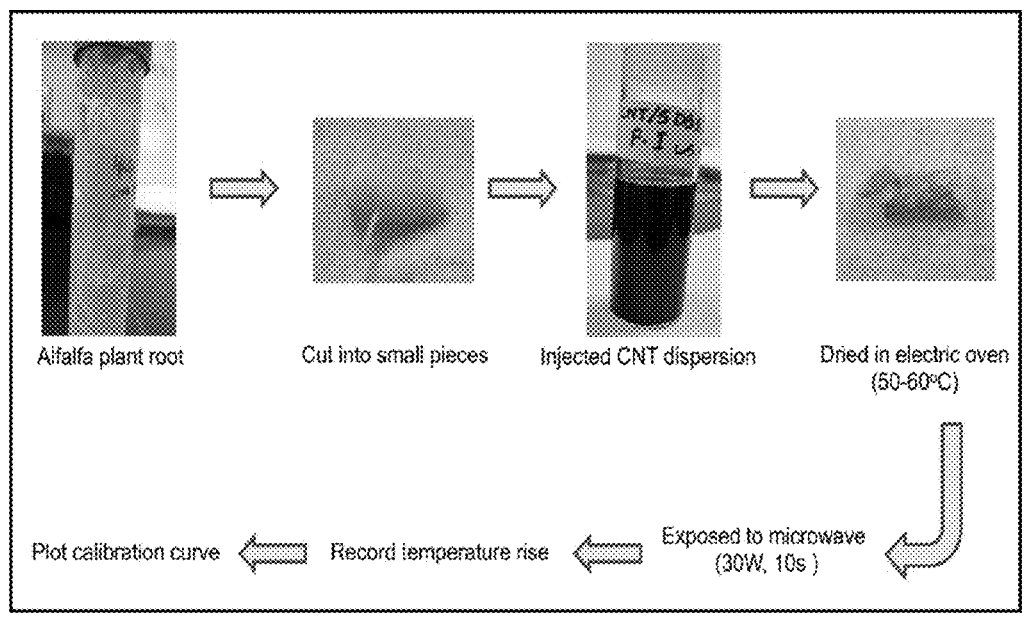
FIG. 2 is a flow diagram of the overall procedure of sample preparation.

Nanotube injected root preparation. Alfalfa (Medicago sativa) roots were taken as a representative root for method development. Alfalfa seeds were germinated and grown for 111 days in control soil (no CNTs in the soil). Plant roots were collected and washed with DI water to remove soil and other particles. The main/primary roots (comparatively fat) were cut into small pieces. A controlled volume (5 μL) of CNT dispersion was injected into the root by a precision syringe (Pressure-Lok Corporation, Series CG-130) to prepare the known samples for the generation of a calibration curve. The mass of CNTs inside the root varied from 0 to 0.8 μg. Both SWCNT and MWCNT injected roots were prepared to investigate the dependence on microwave heating on CNT type. A flow diagram of the overall procedure of sample preparation is shown in FIG. 2.

Dry MWCNTs were mixed into soil to obtain concentrations of 1000 and 10000 mg/kg. Alfalfa seeds were germinated and grown in the CNT-laden soil. The plant roots were collected after 14 days and 111 days of growth, cleaned with DI water, immersed in a bottle containing DI water and stored in the cold. These samples were used as unknown samples to determine the amount of MWCNTs absorbed by the root using our calibration curve.

A variable power microwave generator was connected to a microwave WR-284 waveguide. A ~1 cm hole was drilled on the top of the waveguide to insert the sample holder through it. Two different power levels (30 W and 50 W at 2.45 GHz frequency) were used in all studies. The microwave generator generates the microwave power which is directed towards the sample via the waveguide. A glass sample holder was placed into the hole of the waveguide for microwave exposure. The K-type thermocouple probe was inserted into the sample to measure the temperature change. The temperature was measured with a digital thermometer connected to the thermocouple probe. A continuous flow of nitrogen was applied directly onto the surface of the sample to prevent ignition.

Figure 3:
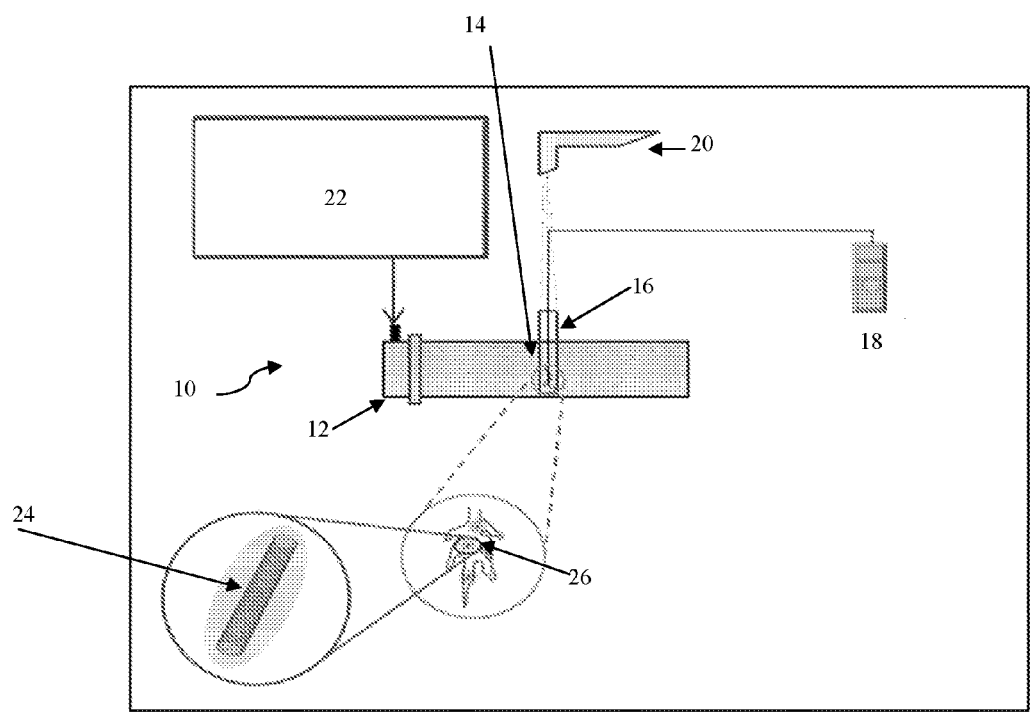
FIG. 3 is a schematic of the setup to detect CNTs in plant roots by microwave absorption.

FIG. 3 is a schematic of the setup to detect CNTs in plant roots by microwave absorption. A magnified view of the root shows elevated temperatures inside the root due to CNT heating during microwave exposure. This setup has some similarity to that of Higginbotham et al. who studied the effects of CNT heating on ceramic sintering except that there is no impedance matched load resistor connected to the waveguide [22].

In one embodiment the device 10 has a body 12 with a sample area 14 to accept a sample chamber 16. The sample chamber 16 is connected to a digital thermometer 18. The digital thermometer 18 can be a k-type thermocouple in some embodiments. A cooling gas 20 is connected to communicate with the sample chamber 16. A microwave power source 22 is connected to the body 12 and waveguides (not shown) to irradiate the sample with a microwave radiation. The CNT 24 is heated by the microwave irradiation to create hot spots in the sample 26.

In this setup, the end of the waveguide was closed with a conducting plate (a short circuit) instead of a matched load. Using a short circuit termination creates a standing wave in the waveguide because of the reflected electromagnetic waves. The electric and magnetic fields of the standing wave will have maxima and minima along the waveguide. The location of the electric field maximum nearest the closed end of the waveguide is a quarter guide wavelength away (wavelength in the waveguide is different than the wavelength in air for the same frequency). This is the position where the ~1 cm hole was drilled to place the sample holder in. The main advantage of this setup is that the electric field magnitude at a location of a maximum is twice that of the matched-load setup. Since the power absorbed by the sample is proportional to the square of the electric field, placing the sample at a location of an electric field maximum requires only a quarter of the power needed in a setup that uses a matched load termination. In other words, much lower power levels are needed in this setup.

A magnified view of CNT heating inside the waveguide is shown in the schematic of FIG. 3. When microwave irradiation is applied, CNTs inside the root sample get heated rapidly due to absorbance of strong microwave power. The reason behind the intensive heating of CNTs due to microwave irradiation is still not understood properly. The commonly accepted mechanism behind this response is dipolar polarization (dielectric heating) [27] which is a strong function of the dielectric constant of materials containing CNTs [15, 23]. This heating of CNTs consequently heats the roots and the temperature rise can be measured by k-type thermocouple. Different amounts of CNTs will heat the roots to different levels. The temperature rise can then be plotted as a function of CNTs present in the roots to generate a calibration curve. Before generating the calibration curve, there are several variable parameters that need to be determined: type of plant and mass of root sample, CNT mass in the sample, microwave power, and exposure time.

Figure 4:
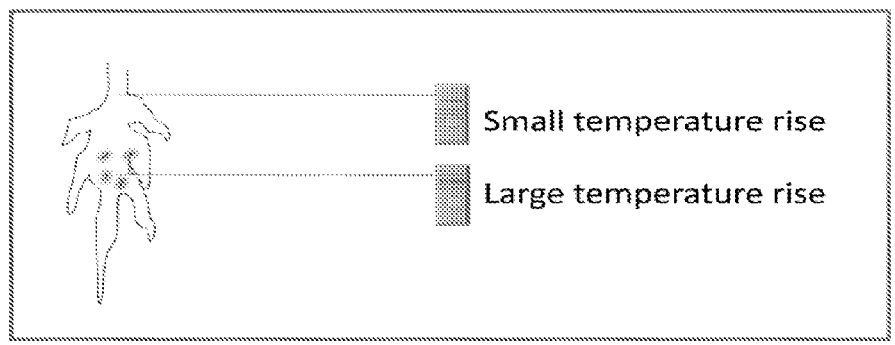
FIG. 4 is an image of the thermocouple placement.

FIG. 4 is an image of the thermocouple placement. As roots are not thermally conductive, thermocouple may not read the actual temperature rise due to CNT heating when it is in contact with a root position where CNT heating effects are lower. This non-uniform heating leads to a variation in temperature measurement for a given sample. For this reason, we reported maximum temperature (most accurate measurement) and also the average and standard deviation plot.

Microwave parameters. Alfalfa (*Medicago sativa*) seeds were germinated in control soil (no CNTs present) and the plant roots were collected after 111 days of growth; they were kept in a refrigerator after immersion in a container full of deionized (DI) water. CNT loaded root samples for the study were prepared by injecting a certain volume of CNT dispersion into small pieces of root (described in studyal section). Root samples were dried properly before microwave exposure. Otherwise the presence of moisture can affect the actual temperature rise when the amount of CNTs present in the sample is very tiny (<0.06 µg). Root samples were dried in a vacuum oven at ~50° C. for 6 hours before performing the microwave studies to ensure that no water or moisture is present in the sample.

To observe the effect of plant type in microwave exposure, two different types of root samples (alfalfa and cotton) were tested. Equal amounts (4.8 mg) of oven dried cotton and alfalfa control roots were exposed to 30 W microwave power for 10 s. The difference between initial and final temperatures gives the actual temperature rise ($\Delta T$) of the sample. For these two samples, the measured $\Delta T$ was in the same temperature range (40-43° C.), which indicates that the type of root does not strongly affect the temperature rise upon microwave exposure. As the microwave heating is not a function of the type of plant, the alfalfa plant root was chosen as a representative root to generate the calibration curve. Table one shows the temperature rise in the same range indicates a weak dependence on root type during microwave exposure (30 W, 10 s).

TABLE 1

| Type of root | Mass of root, mg | Initial T, ° C. | Final T, ° C. | $\Delta T$, ° C. |
|---|---|---|---|---|
| Cotton Root | 4.8 | 25 | 68 | 43 |
| Alfalfa Root | 4.8 | 25 | 65 | 40 |

Other important parameters are the effect of sample mass and CNT mass. To analyze the heating behavior of control roots at a specific microwave power for a certain amount of time, different mass of alfalfa control roots were examined. The effect of mass of roots for long time exposure in microwave was also investigated. Two oven dried alfalfa root samples (4.8 mg and 16 mg) were exposed to constant microwave power (30 W) for long exposure times.

Figure 5:
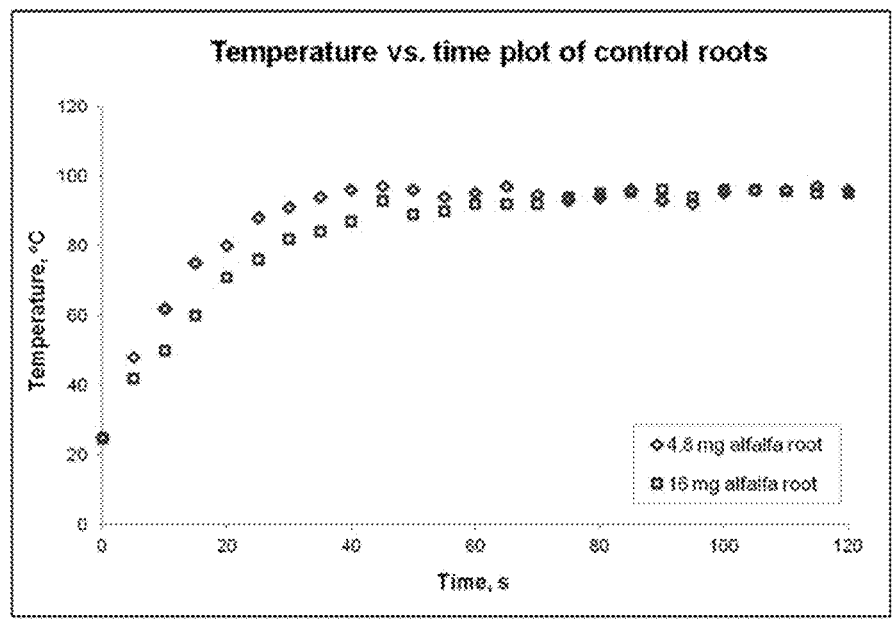
FIG. 5 is a graph that shows the temperature rise for the two samples versus time.

FIG. 5 is a graph that shows the temperature rise for the two samples versus time. Effect of root mass for long exposure time in microwave field. Different amounts of alfalfa plant roots (control roots, no CNT injected) were exposed to 30 W of microwave power, and the temperature rise is plotted against time. This indicates that the temperature rise due to microwave irradiation has a weak dependence on the mass of root of samples. The two curves almost overlap each other after 40 seconds of exposure. The initial discrepancy may occur due to presence of small amount of moisture. In general, this figure shows that the temperature rise due to microwave irradiation is a very weak function of root mass as long as moisture is properly eliminated.

The results are consistent with theoretical expectations because the samples are very small relative to the waveguide dimensions (16 cm×4 cm). The electromagnetic fields at the position of the waveguide, where the sample is placed, can be considered uniform throughout the sample volume. Therefore, variations in mass of such relatively small samples should not affect the temperature rise.

Oven dried alfalfa control roots in the range of 4-20 mg were exposed to 30 and 50 W microwave power for 10 seconds and 6 s, respectively. As the microwave power increases (from 30 W to 50 W), the temperature difference also increases (~40° C. for 30 W to ~60° C. for 50 W). The studyal results indicate that temperature rise ($\Delta T$) depends strongly on microwave power, exposure time, and does not depend on type and mass of root samples. As long as microwave power and exposure time remain constant, $\Delta T$ will be a function of CNTs present inside the root sample. Thus, this technique does not require normalization of CNT mass with the root sample mass. The only parameter that we need to consider in generating the calibration curve is CNT mass injected into the sample. The mass of roots in the prepared known sample for the generation of calibration curve varied between 4-18 mg and the amount of CNTs injected was in the range of 0-0.8 µg.

Generation of calibration curves. Before generating the calibration curve, there are several baseline temperature measurements that must be tested for a given microwave power. These baseline trends include the thermocouple itself, a control root, a sodium dodecyl benzene sulfonate (SDBS) injected sample and single walled carbon nanotube (SWCNT) injected samples.

Figure 6:
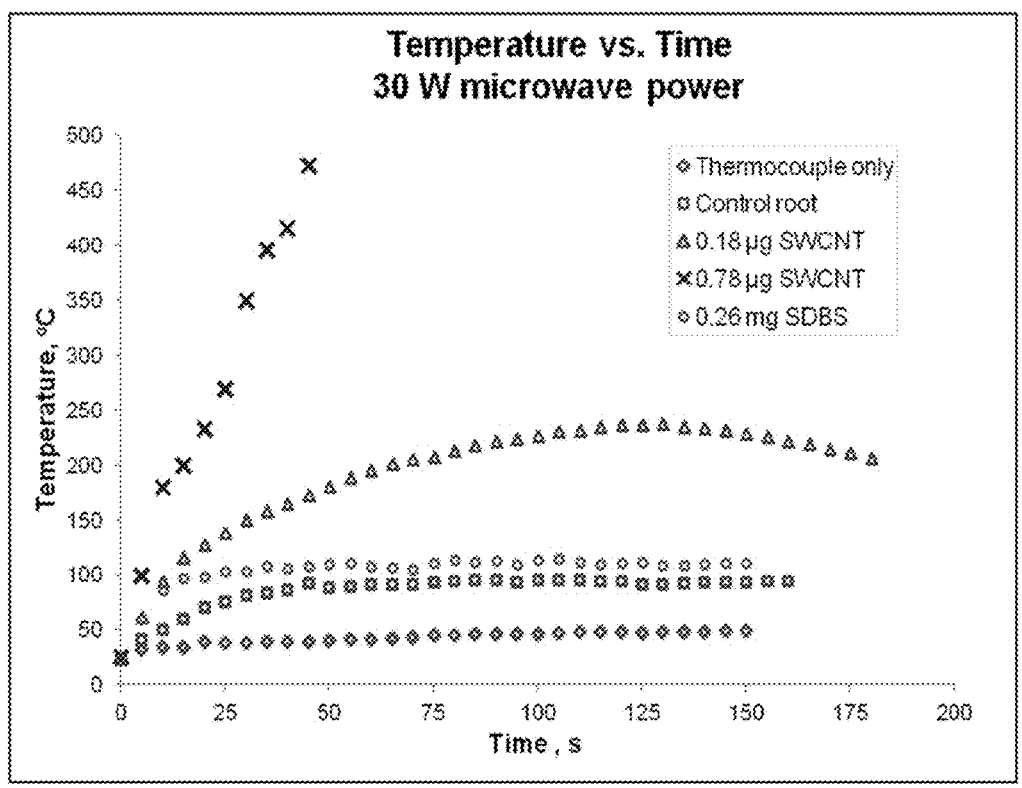
FIG. 6 is a graph that demonstrates the temperature profile for thermocouple, control sample, SDBS injected sample, and different SWCNT loaded samples (0.18 µg and 0.78 µg SWCNT) upon prolonged exposure to 30 W applied microwave power.

FIG. 6 is a graph that demonstrates the temperature profile for thermocouple, control sample, SDBS injected sample, and different SWCNT loaded samples (0.18 µg and 0.78 µg SWCNT) upon prolonged exposure to 30 W applied microwave power. Effects of long time exposure of thermocouple, control root, SDBS injected root and different SWCNT loaded samples to 30 W microwave power. Although the thermocouple, control and SDBS injected root do show heating on their own, the presence of SWCNTs amplifies the temperature rise. When the temperature approaches 300° C., SWCNT ignition occurs, and the temperature approaches ~500° C. within few seconds for 0.78 µg SWCNT injected sample. As the thermocouple probe is metallic, the microwave absorbing properties of the probe was examined by recording the temperature rise while exposing the probe alone in the microwave. The thermocouple heats minimally (maximum ~50° C. for 2 minutes of exposure) compared to the control and CNT injected roots. Although a rise in temperature has been observed for the thermocouple alone and for the control root, they are not significant compared to the temperature rise observed for the 0.18 µg SWCNT-loaded root. For the SWCNT-loaded sample, the temperature steadily rises up to 237° C. after 2 minutes of exposure, and then the temperature decreases due to SWCNT degradation. Note that long (>2 min) microwave exposure times may degrade SWCNTs in contrast to repeated short exposure times ($6^{-10}$ s). After initial rapid rise in temperature, the thermocouple and root samples reached a steady state. However, the root sample with 0.78 µg SWCNT reaches ~500° C. within only 40 seconds of exposure, indicating the ignition of SWCNTs despite a nitrogen blanket. Even if there is continuous flash of nitrogen, it is almost impossible to achieve 100% inert atmosphere inside the sample vial. If the temperature reaches ~300° C., it becomes difficult to prevent the SWCNTs from ignition. Similar behavior was observed for MWCNTs.

To find out the effects of microwave absorption of CNT stabilizer (SDBS) present in the dispersion, 0.26 mg of SDBS was injected (same amount of SDBS when 0.78 µg SWCNT is present in the root) into the root and exposed to the same microwave power (30 W). SDBS injected root sample displayed some increase in temperature rise relative to the control root sample; again, this is not comparable to SWCNT-injected samples. These results indicate that the SWCNT free samples have negligible effects on temperature rise, in comparison with the effects of the SWCNT loaded samples. Calibration curves were generated at different levels of microwave power (30 W and 50 W) for different exposure times (10 seconds and 6 seconds). Both SWCNTs and MWCNTs were evaluated in this study as well.

Figure 7:
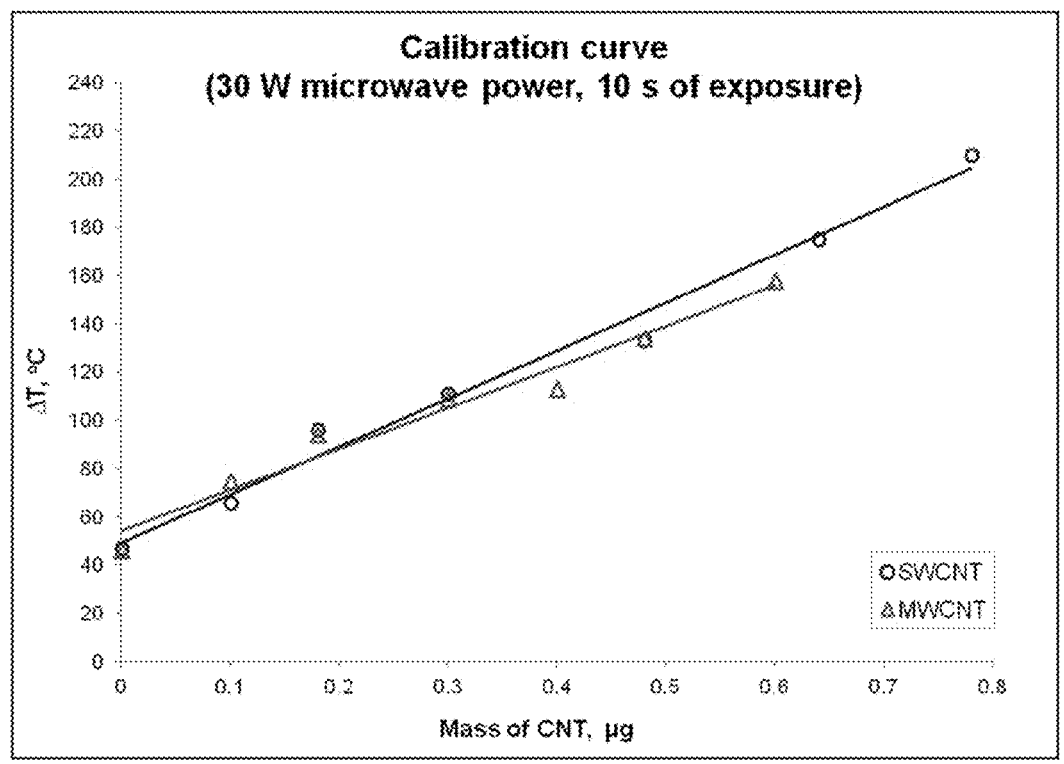
FIG. 7 is a calibration curve generated by using known samples injected with known quantities of CNT (SWCNT and MWCNT) at 30 W microwave power for 10 seconds of exposure.

FIG. 7 is a calibration curve generated by using known samples injected with known quantities of CNT (SWCNT and MWCNT) at 30 W microwave power for 10 seconds of exposure. The root mass of the SWCNT-injected samples varied from 12-18 mg, and MWCNT-injected root mass varied from 4-11 mg.

Figure 8:
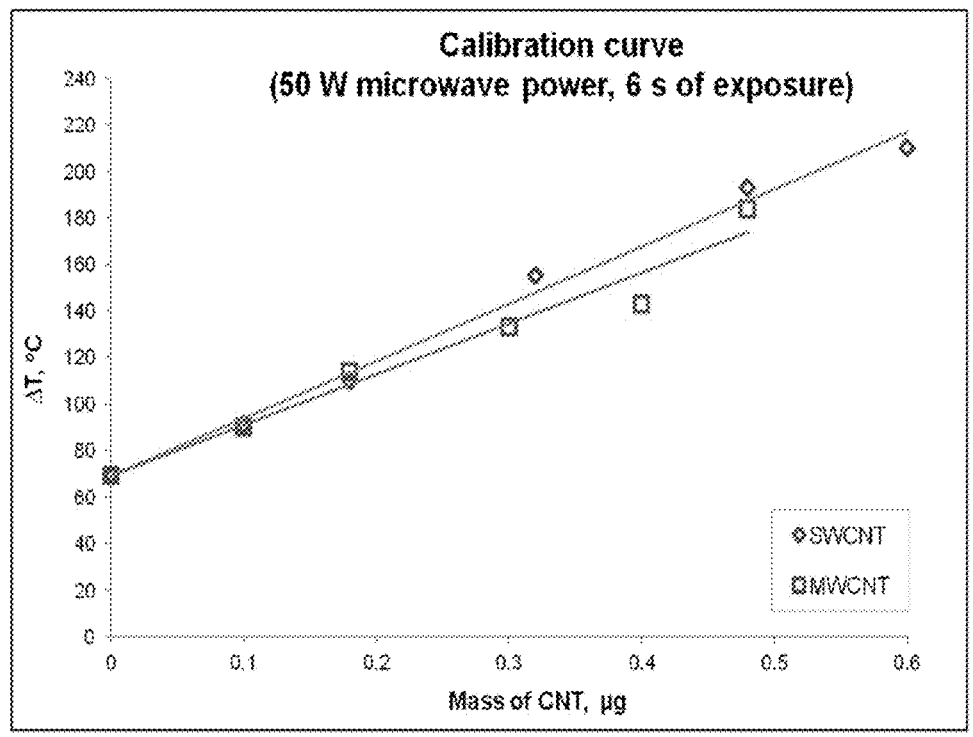
FIG. 8 is a calibration curve generated by using root samples injected with known quantities of CNT (SWCNT and MWCNT) at 50 W microwave power for 6 seconds of exposure.

FIG. 8 is a calibration curve generated by using root samples injected with known quantities of CNT (SWCNT and MWCNT) at 50 W microwave power for 6 seconds of exposure. CNT injected root samples (mass of samples varied from 4-18 mg) were exposed to the microwave and the temperature rise ($\Delta T$) was recorded and plotted as a function of CNT mass (0-0.8 µg). At 50 W applied power for only 6 seconds of exposure in FIG. 8, the measured $\Delta T$ was higher than that of 30 W applied power for 10 seconds in FIG. 6. Again, prolonged exposure of samples in the microwave as seen in FIG. 6 showed that $\Delta T$ increases with time of exposure. Hence, temperature rise of the samples in the microwave has a strong dependence on microwave power and exposure time. As the power or time increases, $\Delta T$ will also increase. These calibration curves also demonstrate that, even the presence of trace amounts of CNTs ($\leq 0.1$ µg) can easily be detected by this technique which is far lower than any other competing methods (SEM, TEM or Raman spectroscopy). The samples were also examined in lower microwave power (15 W) for 20 seconds; at this power level the threshold of detecting CNTs becomes higher as the difference of temperature rise between control sample and smaller CNT loaded samples (0.1-0.18 µg) cannot be distinguished clearly. Since short times (~10 seconds) and higher power (30 W-50 W) are able to quantify the presence of trace amount of CNTs, the detectable threshold can be moved lower simply by raising the microwave power or exposure time associated with a given calibration curve.

The effect of different types of CNTs (SWCNT and MWCNT) is also illustrated in FIGS. 7 and 8. According to the calibration curves (30 W and 50 W), $\Delta T$ is little lower for MWCNT-injected samples than SWCNT loaded samples. However, Higginbotham et al. studied the effect of different types of CNTs loaded in ceramic sample upon microwave exposure and found that MWCNTs display the highest heating compared to SWCNTs and f-SWCNTs. The figure also depicts that initially when the rapid increase in temperature occurs, the SWCNT and MWCNT heats up almost at the same rate [24].

All the samples were tested with the microwave method at least for 10-15 times and the results were replicable within a certain range of temperatures. For temperatures below ~300° C., the samples repeatedly displayed the same heating behavior, indicating that the roots are merely heated and not degraded. In the calibration curves shown in FIGS. 7 and 8, the maximum temperatures found for each sample were considered as we believe that this is the most accurate measurement of the temperature rise. There are a number of factors, including thermocouple placement relative to the root that could yield artificially low values for $\Delta T$. It is also possible that CNT loading (and thus CNT-induced heating) in the root are non-uniform; as roots are not a good thermal conductor, this non-uniform loading creates non-homogeneous heating of the sample, so again, we report maximum readings in the calibration curves. The average and standard deviation for $\Delta T$ measurements were also recorded and plotted in FIGS. 9-15.

Figure 9:
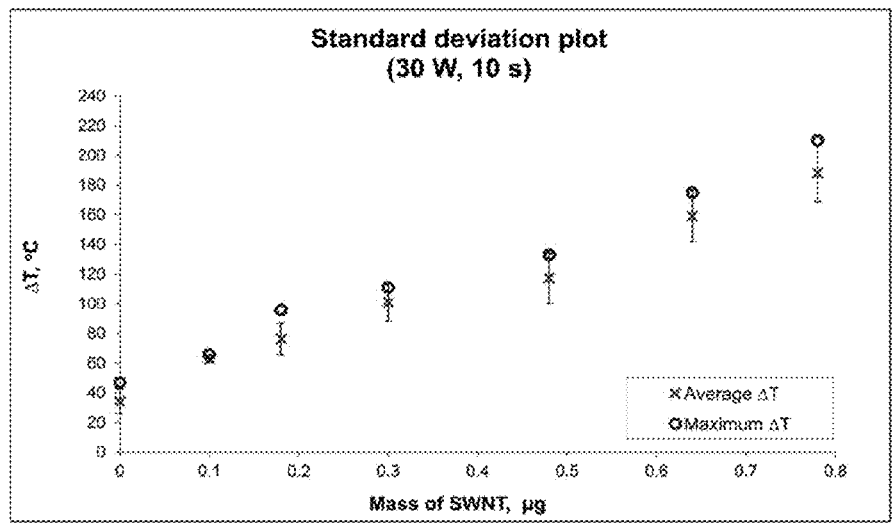
FIG. 9 is a calibration curve of SWNT injected alfalfa root at 30 W microwave power and 10 seconds of exposure with standard deviation.

FIG. 9 is a calibration curve of SWNT injected alfalfa root at 30 W microwave power and 10 seconds of exposure with standard deviation. The average and standard deviation are taken from 10-15 measurements on each sample. Maximum temperature rise is also shown in this figure.

Figure 10:
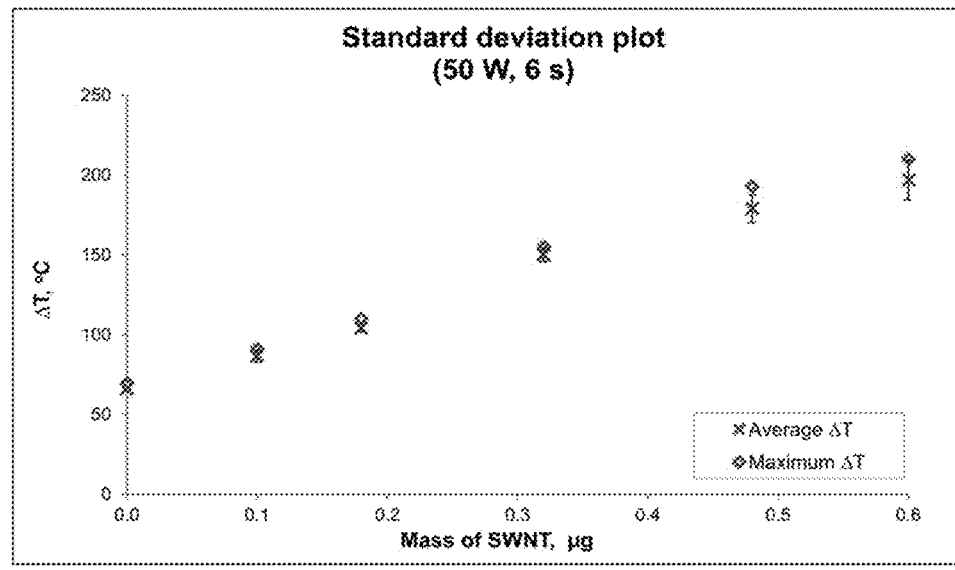
FIG. 10 is a calibration curve of SWNT injected alfalfa root at 50 W microwave power and 6 seconds of exposure with standard deviation.

FIG. 10 is a calibration curve of SWNT injected alfalfa root at 50 W microwave power and 6 seconds of exposure with standard deviation. The average and standard deviation are taken from 8-10 measurements on each sample. The maximum temperature rise is also shown in this figure.

Figure 11:
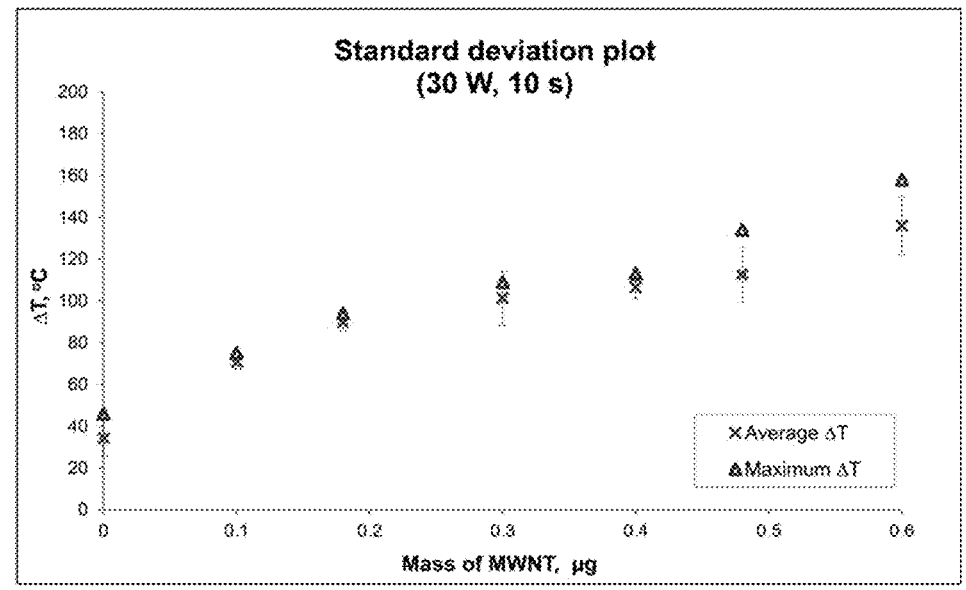
FIG. 11 is a calibration curve of MWNT injected alfalfa root at 30 W microwave power and 10 seconds of exposure with standard deviation.

FIG. 11 is a calibration curve of MWNT injected alfalfa root at 30 W microwave power and 10 seconds of exposure with standard deviation. The average and standard deviation are taken from 8-10 measurements on each sample. The maximum temperature rise is also shown in this figure.

Figure 12:
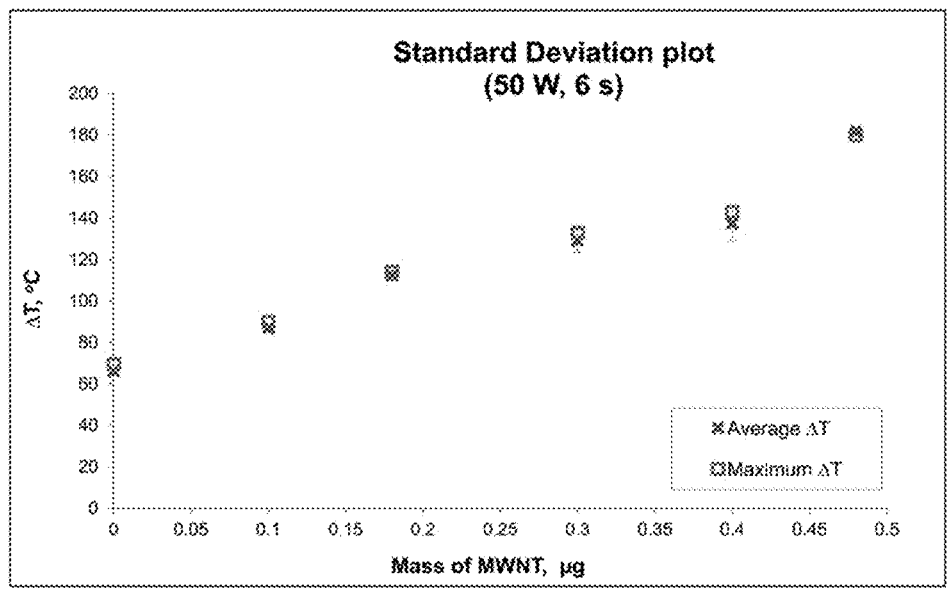
FIG. 12 is a calibration curve of MWNT injected alfalfa root at 50 W microwave power and 6 seconds of exposure with standard deviation.

FIG. 12 is a calibration curve of MWNT injected alfalfa root at 50 W microwave power and 6 seconds of exposure with standard deviation. The average and standard deviation are taken from 5-8 measurements on each sample. The maximum temperature rise is also shown in this figure.

A blind analysis was conducted with seven SWCNT-injected root samples. All the root samples were exposed to 30 W (for 10 s) and 50 W (for 6 s) microwave power; $\Delta T$ measurements were recorded and then analyzed using the calibration curves. Table 2 shows the readings from the calibration curves and also the actual SWCNTs injected into the sample.

TABLE 2

Blind test analysis of SWCNT loaded samples.

| Sample No. | Mass of root, mg | Power, W | Time, s | $\Delta T$, ° C. | Mass of SWCNT, µg (From calibration curve) | Actual SWCNT present, µg |
|---|---|---|---|---|---|---|
| 1 | 1.7 | 30 | 10 | 70 | 0.1 | 0.12 |
|  |  | 50 | 6 | 105 | 0.13 |  |
| 2 | 1.6 | 30 | 10 | 66 | 0.075 | 0.06 |
|  |  | 50 | 6 | 88 | 0.078 |  |
| 3 | 2 | 30 | 10 | 53 | 0 | 0 |
|  |  | 50 | 6 | 67 |  |  |
| 4 | 1.8 | 30 | 10 | 41 | 0 | 0.06 |
|  |  | 50 | 6 | 52 |  |  |
| 5 | 8 | 30 | 10 | 120 | 0.36 | 0.4 |
|  |  | 50 | 6 | 164 | 0.38 |  |
| 6 | 5 | 30 | 10 | 91 | 0.23 | 0.24 |
|  |  | 50 | 6 | 120 | 0.21 |  |
| 7 | 4 | 30 | 10 | 45 | 0 | 0 |
|  |  | 50 | 6 | 54 |  |  |

The results suggest that above 0.1 µg SWCNT present in the sample, two independent measurements yield very similar and almost accurate estimates for the true CNT loading. The uncertainty rises below this threshold. This problem can easily be avoided by using a calibration curve at a higher microwave power or for a longer time at a lower microwave power. These results demonstrate the utility and versatility of the method.

After establishing the reliability of the method, quantitative detection of CNTs on several unknown root samples grown in different CNT-laden soils were conducted. Alfalfa roots were collected from the plants that have been grown in MWCNT laden soil (1000 and 10,000 mg/kg) and taken after 14 and 111 days of growth. The unknown samples were named as sample-A: alfalfa plant grown for 14 days (1000 mg/kg MWCNT in soil), sample-B: alfalfa plant grown for 111 days (1000 mg/kg MWCNT in soil), and sample-C: alfalfa plant grown for 14 days (10,000 mg/kg MWCNT in soil). Raman spectroscopy was performed on these samples to detect the presence of MWCNT. However, Raman spectra showed no indications of CNTs in any of the above samples; of course, such measurements can easily give a false negative, so the presence of CNTs remains unknown. In contrast, our microwave method showed that sample-B adsorbed 0.1 µg (using the 30 W calibration curve) or 0.09 µg (using the 50 W calibration curve) MWCNT in the root; whereas the $\Delta T$ values for samples A and C indicate the absence of MWCNTs according to both calibration curves. This agreement between two individual measurements confirms the reliability of the reading and also confirms that the microwave technique is significantly more sensitive than alternative techniques. The results using different calibration curves (for different microwave power) are presented in Table 3.

TABLE 3

Detection of MWCNT in unknown sample.

| Sample | Mass of root, mg | Power, W | Time, s | $\Delta T$, ° C. | Mass of MWCNT, µg (from calibration curve) |
|---|---|---|---|---|---|
| A | 7 | 30 | 10 | 41 | 0 |
|  |  | 50 | 6 | 53 |  |
| B | 9.8 | 30 | 10 | 71 | 0.1 µg |
|  |  | 50 | 6 | 87 | 0.09 µg |
| C | 5.7 | 30 | 10 | 40 | 0 |
|  |  | 50 | 6 | 59 |  |

Table 3 indicates that the microwave-heating method provides a means to quantify CNTs which may be useful in explaining any observed toxicity with on the actual amount of MWCNTs adsorbed by the plant.

The use of microwave-heating for CNT detection in environmental samples is entirely novel and addresses a wide-ranging obstacle in the field of nanotoxicology. The use of this method is invaluable to effectively quantify CNTs in crop species. The versatility of this technique is not limited to agricultural samples; this is also applicable to other biological and environmental samples.

MWNTs in biological samples can be detected and quantified by microwave induced heating. Freeze drying was a reliable sample processing method for MWNT microwave analysis. Bioaccumulation study indicated low MWNT bioaccumulation in earthworms. Reliable quantification techniques for carbon nanotubes (CNTs) are limited. The present invention provides a new procedure for quantifying multi-walled carbon nanotubes (MWNTs) in biological samples based on freeze drying and microwave-induced heating. For example, earthworms (*Eisenia fetida*) were first processed into a powder by freeze drying. Then, samples were measured by utilizing 10 seconds exposure to 30 W microwave power. This method showed the potential to quantitatively measure MWNTs in earthworms at low concentrations (~0.1 µg in 20 mg of earthworm). Also, a simple MWNT bioaccumulation study in earthworms indicated a low bioaccumulation factor of 0.015±0.004. With an appropriate sample processing method and instrumental parameters (e.g., power and exposure time), this technique has the potential to quantify MWNTs in a variety of sample types (plants, earthworms, human blood, etc.).

With unique chemical, physical, and electrical properties, carbon nanotubes (CNTs) have led to new technologies in various fields (Aitken et al., 2006; de Heer, 2004). Since CNTs are likely to be released into the environment like other industrially important chemicals, there is a need for fate and toxicity studies of CNTs (Lam et al., 2006; Plata et al., 2012). However, quantitative information of CNT fate and toxicity is still scarce. Most studies have been conducted without CNT quantification in environmental matrices (daphnid, zebrafish, plant, soil, etc.) (Alloy and Roberts, 2011; Aschberger et al., 2010; Cañas et al., 2008; Cheng et al., 2007; Zhao and Liu, 2012).

Studies have been conducted to identify CNTs in various environmental media (Leeuw et al., 2007; Plata et al., 2012; Sobek and Bucheli, 2009; Ribeiro et al., 2010; Cerqueira et al., 2011; Silva et al., 2012a; Quispe et al., 2012; Oliveira et al., 2012a; Yang et al., 2011). Near-infrared fluorescence was used to detect CNTs in fruit flies (*Drosophila melanogaster*) and blackworms (*Lumbriculus variegatus*) (Leeuw et al., 2007; Yang et al., 2011). Specifically, Leeuw et al. (2007) estimated that only a very small fraction (about 10-8) of ingested CNTs was incorporated into fruit fly larvae organs. Yang et al. (2011) reported a bioaccumulation factor (BAF) of 0.0021±0.0011, which indicated that blackworms could not accumulate CNTs. However, these techniques are only applicable for unbundled single-walled carbon nanotubes (SWNTs) (Leeuw et al., 2007; Yang et al., 2011).

There are several other CNT bioaccumulation studies based on carbon-14 labeled CNTs (Petersen et al., 2008, 2009a). Low BAF values were also reported in earthworms raised in two types of soil both contaminated with different CNTs (Petersen et al., 2008, 2009a) and the majority of the accumulated CNTs remained in the guts rather than adsorbed into cellular tissues of Daphnia magna (Petersen et al., 2009a). Most of the CNT analyses to date have been conducted with a radiolabeled technique (Petersen et al., 2008, 2009b). While radio-labeled technique aids lab-based research with CNTs because of the simplicity of CNT quantification by radiolabeling them, the majority of CNTs used in the real world are not radiolabeled. The radiolabeled technique could not be used to detect non-radiolabeled CNTs present in field samples (ex. earthworms in CNT contaminated field soil). A chemothermal oxidation method at 375° C. (CTO-375) has been used to isolate CNTs in soils and sediments (Sobek and Bucheli, 2009). However, analytical method parameters, such as detection limit and quantification limit were not reported. A recent study by Plata et al. (2012) used thermogravimetric analysis (TGA) to detect tiny amounts of SWNTs (e.g., 100 µg SWNT per g of sediment) in various complex mixtures. This analysis also requires mass spectrometry to determine the amount of SWNTs present in the environmental matrices. However, co-degradation of SWNTs along with other carbonaceous material can evolve similar gasses at the same temperature in TGA, which may lead to erroneous conclusions if the mass spectrometer is not sensitive enough to distinguish the SWNT degradation peak. Due to the strong absorption of microwaves, CNTs can generate large amounts of heat within a very short time (Irin et al., 2012).

This unique CNT property has been applied in a variety of fields (Brunetti et al., 2007; Shim et al., 2009). Recently, a novel method based on microwave-induced heating was successfully used to quantify CNT concentrations in plant roots Grin et al., 2012). CNT masses in plant roots were correlated with a temperature change when samples were exposed to microwaves. The detectable threshold limit of CNTs in plant roots by this technique was less than 0.1 µg, which is closer to the expected environmental conditions than the detection limits of other conventional methods (e.g., electron microscopy with scanning electron microscope, Raman spectroscopy, fluorescence, Mössbauer spectroscopic, Automated Scanning Electron Microscope Image Analysis, etc.) (Cerqueira et al., 2012; Silva et al., 2011a,b). As with traditional contaminants, CNTs might be released into various environmental compartments and potentially pose a risk to various organisms. For the broad application of this technique, it is necessary to develop an efficient sample processing technique and explore suitable instrumental parameters to quantify CNTs in different environmental matrices. With the aid of a new sample processing method (e.g., freeze drying) for microwave-induced heating, the present invention also expanded this technique to quantify multi-walled carbon nanotube uptake in earthworms (*Eisenia fetida*), a commonly used model organism in environmental studies.

Multi-walled carbon nanotubes (MWNTs) were purchased from Cheap Tubes Inc. (Brattleboro, Vt.). MWNT outer diameters ranged from 30 to 50 nm and length ranged from 10 to 20 µm with >95 wt % purity and b1.5 wt % ash content. Sodium dodecyl benzene sulfonate (SDBS; MW: 348.5) was purchased from Sigma Aldrich (Allentown, Pa.). All of these materials were used without any further purification. Adult earthworms (*E. fetida*) were purchased from Yelm Earthworm and Castings Farm (Yelm, Wash.). Sandy loam soil (Lubbock, Tex.) was prepared by sieving through a 2-mm sieve. The physicochemical properties of soil were determined by AGVISE Laboratories (Northwood, N. Dak.). The soil (pH=7.8, organic carbon content=1.1%) consisted of 74% sand, 16% silt, and 10% clay.

A stable MWNT dispersion was prepared by sonication and centrifugation using SDBS as a stabilizer (Green, 2010). SDBS (2% w/v) was completely dissolved in water by magnetic stirring and 1 mg/mL of MWNTs was added to this solution. This mixture was then tip sonicated for 1 hour at an output power of 7 W (Misonix sonicator, XL 2000) and centrifuged (Centrific Centrifuge 225, Fischer Scientific) for 4 hours at a speed of 5000 rpm. After centrifugation the supernatant was collected and absorbance was measured with a Shimadzu UV-vis spectrophotometer 2550 at wavelengths of 200 nm to 800 nm. The concentration of the dispersion was calculated from the absorbance (at 660 nm) using the Lambert-Beer law. The extinction coefficient was taken as 3389 mL/mg·m (Amiran et al., 2008). The final concentration of the dispersion was 0.3 mg/mL MWNTs (Irin et al., 2012). Note that the MWNT dispersion was made to prepare the known earthworm calibration samples, not for mixing with the soil, which is described below.

Dead earthworms were frozen in a freezer at −15° C. to perform freeze drying which was necessary to eliminate the liquid (mostly water) inside the earthworm since the presence of water can affect the temperature measurements needed in the microwave-induced heating method. Freeze drying was conducted in a Virtis Benchtop Freeze Dryer for 1 day. Dried earthworms were then crushed into a powder. A controlled volume of MWNT dispersion was mixed with 20 mg of earthworm powder with a micro pipette (0-10 µL) to prepare the known samples for the generation of a calibration curve.

The mass of MWNTs in the samples varied from 0 to 3.2 μg. Earthworm mass was kept constant for all the samples to avoid the effect of sample mass on the microwaves. These samples were dried overnight in a vacuum oven at 60° C. before conducting the microwave analysis.

A variable microwave power generator (Opthos Instruments Inc., MPG 4 RF, LAB-909) was connected to a rectangular WR-284 waveguide. This generator can generate microwave power from 0 to 120 W with a resolution of 1 W. The operating frequency of the generator was 2.45 GHz. The sample holder was inserted into the waveguide through a ~1 cm hole drilled on the top. The waveguide directed the power towards the sample and heated MWNTs as well as the sample. The temperature rise of the sample was then measured by a digital multimeter (Omega model HHM290) which was connected to a K-type thermocouple (Omega Model SC-GG-K-30-36, ungrounded, 0.032" diameter). A continuous flow of nitrogen was applied directly onto the surface of the sample to prevent MWNT ignition.

Previous studies reported low bioaccumulation of MWNTs in earthworms exposed to 0.03-0.5 mg/g MWNTs in contaminated soil (Petersen et al., 2008, 2009b, 2011). Unlike traditional contaminants, higher concentrations of MWNTs in soil might lead to lower bioaccumulation due to an increased MWNT aggregation which would ultimately decrease the ability of MWNTs to cross cellular barriers. This study used 3 mg/g MWNTs in soil in order to examine if a higher MWNT concentration would lead to lower MWNT bioaccumulation in earthworms.

In order to achieve the homogeneity of MWNT distribution in soil, soil (20 g) was spiked with 60 mg dry MWNTs similar with a previous method (Petersen et al., 2009b). Note that the homogeneity of MWNTs in soil was not tested by the microwave-based detection technique; a method for soil is currently under development. Soil (20 g) in a rotating container was spiked with dry MWNTs by the addition of small volumes at a time. After MWNTs were completely mixed into the soil, the soil container was sealed and tumbled overnight. Then the mixture was placed in 8-oz amber glass jars. There were 12 jars containing MWNTs and 4 control jars without MWNTs. Controls were used to check for any possible interference. One adult earthworm (0.8-0.9 g) was placed in each jar, including the controls. Teflon-lined lids were used to loosely cover the jars. Deionized water was dropped on top of the soil every day to maintain constant moisture (30% of water holding capacity). Studies were conducted in the dark at 18-22° C. Earthworms were removed from triplicate jars containing MWNTs as well as from one control jar on days 1, 7, 14, and 28. Following a 24 hours depuration period on filter paper, worms were washed, weighed, and stored in a refrigerator at −20° C. until freeze drying. After exposure in soil contaminated with 3 mg/g MWNTs for 14 d, a parallel elimination study was also conducted in CNT-free soil. Earthworms were removed on days 1, 5, and 7.

Uptake data were fit to a one-compartment first-order toxicokinetic model (Landrum et al., 1992; Liu et al., 2008). The following equation was used:

$$C_t = \frac{k_u}{k_g} C_0 (1 - e^{-k_z t}).$$

Where $C_t$ was the MWNT concentration in earthworms at time t (mg/kg·w/w), $C_0$ was the initial MWNT concentration in soil (μg/g), $k_u$ (μg/g·d) was the uptake coefficient of MWNTs from soil, and $k_e$ (μg/g·d) was the elimination rate constant of MWNTs from soil. The modeled bio accumulation factor (BAF) was calculated as:

$$BAF = \frac{k_u}{k_g}.$$

In order to quantify CNT content inside earthworms, a calibration curve was generated based on the microwave detection technique. The procedure for developing the calibration curve was similar to a prior study with the main difference being the matrix (freeze dried powder of earthworm sample vs. whole plant roots) (Irin et al., 2012). Powdered samples were preferred over structurally intact earthworm samples in order to achieve better contact with the thermocouple probe and to obtain repeatable temperature readings. Moreover, injection of a controlled volume of MWNT dispersion into an intact earthworm sample could result in a non-uniform distribution since MWNTs may be confined to the point of injection. Instead, the addition of an MWNT dispersion to a powdered sample ensured a uniform mixture. Both whole worms and powdered worms were tested in the microwave setup; the powdered samples generated far more consistent, repeatable results than intact earthworm samples. The most important parameters to select for the microwave technique are the microwave power and exposure time. The microwave power and exposure time must be high enough to generate a significant temperature rise in an MWNT-injected sample; however, overexposure may cause sample degradation. Based on these considerations, the study was performed at 30 W microwave power for 10 seconds of exposure. Longer exposure times (30 W, 20 s) and higher power (50 W, 10 seconds) was investigated as well, but these parameters suffered from sample degradation as described above.

Figure 13:
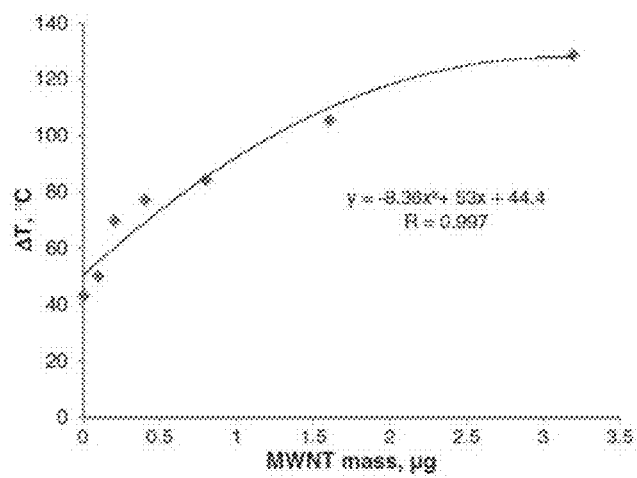
FIG. 13 is a graph that demonstrates the microwave-induced heating calibration curve for earthworms.

FIG. 13 is a graph that demonstrates the microwave-induced heating calibration curve for earthworms. Samples (20 mg of powdered earthworms) were exposed to 30 W microwave power for 10 s. Each sample was tested at least five times for statistical analysis. However, the maximum value of the temperature rise found for each sample was considered to generate the calibration curve; based on the previous study, the highest temperature rise was the most accurate measurement of the actual temperature for a given sample Grin et al., 2012). The studyal data was fitted to a polynomial equation with an R2 value of 0.997. The calibration curve showed a plateau at higher loading of MWNTs in the sample; the reason for this is that it represents the maximum capacity of the sample to absorb heat. As the loading of MWNTs increases in a given sample, the total amount of heat absorbed by the MWNTs as well as by the sample nears saturation. If this heat energy is represented by Q=mCpΔT, then, ΔT will be almost the same at high loadings even if there is a little difference in CNT mass (m) present inside the sample (Cp is the specific heat capacity of CNT which is assumed constant).

As a result, the calibration curve will appear to plateau at a high loading. Reliability and accuracy of this technique were confirmed by a set of proof-of-concept studies similar to those in Irin et al. (2012). The microwave-induced heating method was shown to be reliable for the quantification of MWNTs in earthworms. The microwave-induced heating method proved to be a reliable tool for MWNT quantification in earthworm tissues. The method reporting limit for MWNTs (0.1 μg/20 mg earthworm sample) at 30 W microwave power and 10 seconds of exposure time was still high. However, with future improvement, this method has been a promise to be a tool for the quantification of MWNTs at environmentally relevant concentrations. In fact, the threshold limit can be optimized by selecting proper microwave power and exposure time; a higher microwave power or a longer exposure time with lower microwave power will be especially helpful if degradation of the sample due to MWNT ignition can be avoided by creating a perfectly inert environment. Future work will be focused on the improvement of this technique since this method is one of the most sensitive MWNT detection tools to date. Another concern regarding the detection limit might be the presence of other carbonaceous materials in soil that may interfere with the temperature rise following exposure tomicrowaves. The presence of carbon black or other carbon based materials in control samples might interfere with the temperature reading. However, such an effect was not observed in the control earthworm samples in this study which implies that those materials have no or minimal response due to microwave exposure. The previous study also confirmed that other materials, such as carbon black, and graphite, have a much slower response in microwaves compared to MWNTs (Irin et al., 2012).

Figure 14:
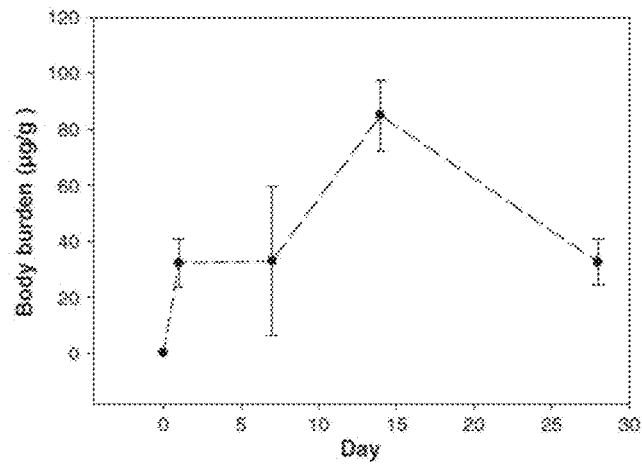
FIG. 14 is a graph that demonstrates the uptake of MWNTs in soil by earthworms after 28 days.

FIG. 14 is a graph that demonstrates the uptake of MWNTs in soil by earthworms after 28 days. Earthworms grown in MWNT-contaminated soil were collected and tested using the microwave-heating technique. The uptake of MWNTs was correlated with the temperature rise of the samples using the calibration curve. Twenty-five earthworm samples (with four controls) in total were investigated for the bioaccumulation study. The uptake of MWNTs by earthworms is shown in FIG. 14. Uptake of MWNTs in soil by earthworms after 28 d. Error bars represent one standard error (n=3). Samples with dead worms were excluded (n=2 on day 7). Body burden of MWNTs (μg) in dry earthworm mass (g) is reported. Earthworms had a tendency to take up MWNTs, with a maximum body burden of 85±13 μg/g on day 14. However, MWNT body burden in earthworms decreased to 33±8.3 μg/g on day 28. In order to further examine if earthworms could eliminate MWNTs, earthworms were transferred into clean soil after a 14 d MWNT exposure.

Figure 15:
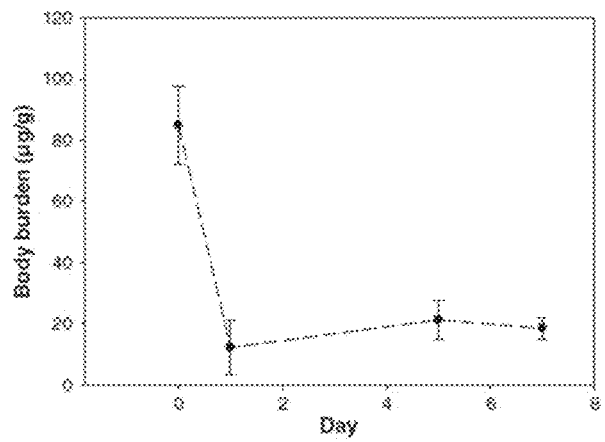
FIG. 15 is a graph that demonstrates the earthworm elimination of MWNTs following a 14 day exposure in soil.

FIG. 15 is a graph that demonstrates the earthworm elimination of MWNTs following a 14 day exposure in soil. Error bars represent one standard error (n=3). Samples with dead worms were excluded (n=2 on day 1). Body burden of MWNTs (μg) in dry earthworm mass (g) is reported. Earthworms had the tendency to depurate MWNTs very quickly. The MWNT concentration in earthworms (85±13 μg/g on day 14) decreased to 21±6 μg/g by day 5 of elimination. In order to better evaluate the bioaccumulation behavior of MWNTs in earthworms, a BAF was calculated based on estimated ku (325±81 μg/g/d) and ke (21330±100 μg/g/d) values. The calculated BAF was 0.015±0.004. Interestingly, a previous study observed a similar BAF for radiolabeled MWNTs in earthworms (Petersen et al., 2008). Specifically, a BAF of 0.014±0.003 was reported in a similar soil mixed with 0.3 mg/g MWNTs. These low BAFs both indicate that apparent uptake of MWNTs in earthworms might be caused by MWNTs in soil remaining in the worm guts after 24 hours depuration (Petersen et al., 2008) and not absorbed MWNTs.

Several previous studies also reported that earthworms showed minimal uptake of MWNTs and they could readily eliminate any accumulated MWNTs (Petersen et al., 2010, 2011). Earthworms exposed in clean soil were also analyzed for a possible false positive reading with the microwave-induced heating method. No heat generation above the detection limit was observed for control earthworm sample on days 1, 7 and 14. However, an unexpectedly high heat response was detected in one control sample on day 28. Given the consistent lack of MWNT detection in other control samples, it is possible that either soil from the sample on day 28 or the sample itself was accidently contaminated with naturally occurring or engineered carbon nanomaterials. When exposed to highly MWNT-contaminated soil, earthworms had a low tendency to bioaccumulate MWNTs, indicated by the low BAF value. Nonetheless, more work is needed to fully understand the bioaccumulation and related toxicity of CNTs for the following reasons: (1) CNTs vary in physicochemical properties (multi- vs. single-walled, size, length, surface area, and functional group) which could lead to differential bioaccumulation and toxicity behaviors (Cañas et al., 2008; Petersen et al., 2008; Zhao and Liu, 2012), (2) different organisms with different physiological behaviors and habitats could have different sensitivities to CNTs, and (3) physicochemical properties (environment characteristics, pH/Eh, and ionic strength) of the environment in which CNTs are released into can also have an impact on CNT fate and behavior (Oliveira et al., 2012b; Silva et al., 2012b,c,d). For example, pH and ionic strength could affect the dispersion state of highly functionalized CNTs. It was reported that COOH-functionalized CNTs were only stable and dispersed in aqueous solutions of pH 5-11 (Shieh et al., 2012). 4. Conclusion By coupling freeze drying with microwave-induced heating, this study developed a novel and reliable analytical procedure for quantifying MWNTs in earthworms. By utilizing 10 seconds of exposure to 30 W microwave power, this technique quantified MWNTs in earthworms at low concentrations (~0.1 μg in 20 mg of earthworm). In addition, a simple study of MWNT bioaccumulation in earthworms in soil indicated a similar BAF value as previously reported studies based on radiolabeled techniques.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine studyation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue studyation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] Iijima S. Helical Microtubules of Graphitic Carbon. Nature. 1991 Nov. 7; 354(6348):56-8.

[2] Green M J, Behabtu N, Pasquali M, Adams W W. Nanotubes as Polymers. Polymer. 2009; in press, 10.1016/j.polymer.2009.07.044.

[3] Yang K, Zhu L Z, Xing B S. Adsorption of Polycyclic Aromatic Hydrocarbons by Carbon Nanomaterials. Environmental Science & Technology. 2006 Mar. 15; 40(6):1855-61.

[4] Masciangioli T, Zhang W X. Environmental Technologies at the Nanoscale. Environmental Science & Technology. 2003 Mar. 1; 37(5):102A-8A.

[5] Navarro E, Baun A, Behra R, Hartmann N B, Filser J, Miao A-J, et al. Environmental Behavior And Ecotoxicity Of Engineered Nanoparticles To Algae, Plants, And Fungi. Ecotoxicology. 2008 July; 17(5):372-86.

[6] Canas J E, Long M Q, Nations S, Vadan R, Dai L, Luo M X, et al. Effects Of Functionalized And Nonfunctionalized Single-Walled Carbon Nanotubes On Root Elongation Of Select Crop Species. Environmental Toxicology and Chemistry. 2008; 27(9):1922-31.

[7] Khodakovskaya M, Dervishi E, Mahmood M, Xu Y, Li Z R, Watanabe F, et al. Carbon Nanotubes Are Able To Penetrate Plant Seed Coat And Dramatically Affect Seed Germination And Plant Growth. Acs Nano. 2009 October; 3(10):3221-7.

[8] Liu Q, Chen B, Wang Q, Shi X, Xiao Z, Lin J, et al. Carbon Nanotubes As Molecular Transporters For Walled Plant Cells. Nano Letters. 2009 March; 9(3):1007-10.

[9] Kang S, Herzberg M, Rodrigues D F, Elimelech M. Antibacterial Effects Of Carbon Nanotubes: Size Does Matter. Langmuir. 2008 Jul. 1; 24(13):6409-13.

[10] Khodakovskaya M V, de Silva K, Nedosekin D A, Dervishi E, Biris A S, Shashkov E V, et al. Complex Genetic, Photothermal, And Photoacoustic Analysis Of Nanoparticle-Plant Interactions. Proceedings of the National Academy of Sciences of the United States of America. 2011 Jan. 18; 108(3):1028-33.

[11] Leeuw T K, Reith R M, Simonette R A, Harden M E, Cherukuri P, Tsyboulski D A, et al. Single-Walled Carbon Nanotubes In The Intact Organism: Near-IR Imaging And Biocompatibility Studies In Drosophila. Nano Letters. 2007 September; 7(9):2650-4.

[12] Yang M, Kwon S, Kostov Y, Rasooly A, Rao G, Ghosh U. Study of the Biouptake of Labeled Single-Walled Carbon Nanotubes Using Fluorescence-Based Method. Environmental Chemistry Letters. 2011 June; 9(2):235-41.

[13] Imholt T J, Dyke C A, Hasslacher B, Perez J M, Price D W, Roberts J A, et al. Nanotubes In Microwave Fields: Light Emission, Intense Heat, Outgassing, And Reconstruction. Chemistry of Materials. 2003 October; 15(21):3969-70.

[14] Shim H C, Kwak Y K, Han C S, Kim S. Enhancement of Adhesion between Carbon Nanotubes and Polymer Substrates Using Microwave Irradiation. Scripta Materialia. 2009 July; 61(1):32-5.

[15] Wang L, Dang Z M. Carbon Nanotube Composites with High Dielectric Constant at Low Percolation Threshold. Applied Physics Letters. 2005 July; 87(4).

[16] Shim H C, Song J-W, Kwak Y K, Kim S, Han C-S. Preferential Elimination of Metallic Single-Walled Carbon Nanotubes Using Microwave Irradiation. Nanotechnology. 2009 Feb. 11; 20(6).

[17] Ko F H, Lee C Y, Ko C J, Chu T C. Purification Of Multi-Walled Carbon Nanotubes Through Microwave Heating Of Nitric Acid In A Closed Vessel. Carbon. 2005; 43(4):727-33.

[18] Chowdhury S R, Chen Y, Wang Y, Mitra S. Microwave-Induced Rapid Nanocomposite Synthesis Using Dispersed Single-Wall Carbon Nanotubes As The Nuclei. Journal of Materials Science. 2009 March; 44(5):1245-50.

[19] Economopoulos S P, Pagona G, Yudasaka M, Iijima S, Tagmatarchis N. Solvent-Free Microwave-Assisted Bingel Reaction In Carbon Nanohorns. Journal of Materials Chemistry. 2009; 19(39):7326-31.

[20] Brunetti F G, Herrero M A, Munoz J D M, Giordani S, Diaz-Ortiz A, Filippone S, et al. Reversible Microwave-Assisted Cycloaddition Of Aziridines To Carbon Nanotubes. Journal of the American Chemical Society. 2007 November; 129(47):14580-+.

[21] Brunetti F G, Herrero M A, Munoz J D, Diaz-Ortiz A, Alfonsi J, Meneghetti M, et al. Microwave-Induced Multiple Functionalization Of Carbon Nanotubes. Journal of the American Chemical Society. 2008 June; 130(25):8094-100.

[22] Higginbotham A L, Moloney P G, Waid M C, Duque J G, Kittrell C, Schmidt H K, et al. Carbon Nanotube Composite Curing Through Absorption Of Microwave Radiation. Composites Science and Technology. 2008 December; 68(15-16):3087-92.

[23] Li Y-H, Lue J-T. Dielectric Constants Of Single-Wall Carbon Nanotubes At Various Frequencies. Journal of Nanoscience and Nanotechnology. 2007 September; 7(9):3185-8.

[24] Mashal A, Sitharaman B, Li X, Avti P K, Sahakian A V, Booske J H, et al. Toward Carbon-Nanotube-Based Theranostic Agents For Microwave Detection And Treatment Of Breast Cancer Enhanced Dielectric And Heating Response Of Tissue-Mimicking Materials. Ieee Transactions on Biomedical Engineering. 2010; 57(8):1831-4.

[25] Green M J. Analysis And Measurement Of Carbon Nanotube Dispersions: Nanodispersion Vs. Macrodispersion. Polymer International. 2010; in press:DOI 10.1002/pi.2878.

[26] Amiran J, Nicolosi V, Bergin S D, Khan U, Lyons P E, Coleman J N. High Quality Dispersions Of Functionalized Single Walled Nanotubes At High Concentration. Journal of Physical Chemistry C. 2008 March; 112(10):3519-24.

[27] Vazquez E, Prato M. Carbon Nanotubes And Microwaves: Interactions, Responses, And Applications. Acs Nano. 2009 December; 3(12):3819-24.

[28] Aitken R J, Chaudhry M Q, Boxall A B A, Hull M. Manufacture and use of nanomaterials: current status in the UK and global trends. Occup Med 2006; 56:300-6.

[29] Alloy M M, Roberts A P. Effects of suspended multi-walled carbon nanotubes on daphnid growth and reproduction. Ecotoxicol Environ Saf 2011; 74:1839-43.

[30] Amiran J, Nicolosi V, Bergin S D, Khan U, Lyons P E, Coleman J N. High quality dispersions of functionalized single walled nanotubes at high concentration. J Phys Chem C 2008; 112:3519-24.

[31] Aschberger K, Christensen F M, Johnston H J, Stone V, Aitken R J, Hankin S M, et al. Review of carbon nanotubes toxicity and exposure-appraisal of human health risk assessment based on open literature. Crit Rev Toxicol 2010; 40:759-90.

[32] Brunetti F G, Herrero M A, Muñoz JdeM, Giordani S, Díaz-Ortiz A, Filippone S, et al. Reversible microwave-assisted cycloaddition of aziridines to carbon nanotubes. J Am Chem Soc 2007; 129:14580-1.

[33] Cañas J E, Long M, Nations S, Vadan R, Dai L, Luo M. Effects of functionalized and nonfunctionalized single-walled carbon nanotubes on root elongation of select crop species. Environ Toxicol Chem 2008; 27:1922-31.

[34] Cerqueira B, Vega F A, Serra C, Silva L F O, Andrade M L. Time of flight secondary ion mass spectrometry and high-resolution transmission electron microscopy/energy dispersive spectroscopy: a preliminary study of the distribution of Cu2+ and Cu2+/Pb2+ on a Bt horizon surfaces. J Hazard Mater 2011:422-31.

[35] Cerqueira B, Vega F A, Silva L F O, Andrade L. Effects of vegetation on chemical and mineralogical characteristics of soils developed on a decantation bank from a copper mine. Sci Total Environ 2012; 421-422:220-9.

[36] Cheng J, Flahaut E, Cheng S H. Effect of carbon nanotubes on developing zebrafish (*Danio rerio*) embryos. Environ Toxicol Chem 2007; 26:708-16.

[37] De Heer W A. Nanotubes and the pursuit of applications. MRS Bull 2004; 29:281-5.

[38] Green M J. Analysis and measurement of carbon nanotube dispersions: nanodispersion versus macrodispersion. Polym Int 2010; 59:1319-22.

[39] Irin F, Shrestha B, Canas J E, Saed M A, Green M J. Detection of carbon nanotubes in biological samples through microwave-induced heating. Carbon 2012; 50:4441-9.

[40] Lam C-w, James J, McCluskey R, Arepalli S, Hunter R. A review of carbon nanotube toxicity and assessment of potential occupational and environmental health risks. Crit Rev Toxicol 2006; 36:189-217.

[41] Landrum P F, Lydy M J, Lee H. Toxicokinetics in aquatic systems: model comparisons and use in hazard assessment. Environ Toxicol Chem 1992; 11:1709-25.

[42] Leeuw T K, Reith R M, Simonette R A, Harden M E, Cherukuri P, Tsyboulski D A, et al. Single-walled carbon nanotubes in the intact organism: near-IR imaging and biocompatibility studies in drosophila. Nano Lett 2007; 7:2650.

[43] Liu Z, Dai H, Davis C, Cai W, He L, Chen X. Circulation and long-term fate of functionalized, biocompatible single-walled carbon nanotubes in mice probed by Raman spectroscopy. Proc Natl Acad Sci USA 2008; 105:1410-5.

[44] Oliveira M L S, Ward C R, French D, Hower J C, Querol X, Silva L F O. Mineralogy and leaching characteristics of beneficiated coal products from Santa Catarina, Brazil. Int J Coal Geol 2012a; 94:314-25.

[45] Oliveira M L S, Ward C R, Izquierdo M, Sampaio C, deBrum I A S, Kautzmann R M, et al. Chemical composition and minerals in pyrite ash of an abandoned sulphuric acid production plant. Sci Total Environ 2012b; 430:34-47.

[46] Petersen E J, Huang Q, Weber J W J. Bioaccumulation of radio-labeled carbon nanotubes by Eisenia foetida. Environ Sci Technol 2008; 42:3090.

[47] Petersen E J, Akkanen J, Kukkonen J V K, Weber W J. Biological uptake and depuration of carbon nanotubes by Daphnia magna. Environ Sci Technol 2009a; 43:2969-75.

[48] Petersen E J, Pinto R A, Landrum P F, Weber J W J. Influence of carbon nanotubes on pyrene bioaccumulation from contaminated soils by earthworms. Environ Sci Technol 2009b; 43:4181-7.

[49] Petersen E J, Weber Jr W J, Huang Q. Relevance of octanol-water distribution measurements to the potential ecological uptake of multi-walled carbon nanotubes. Environ Toxicol Chem 2010; 29:1106-12.

[50] Petersen E J, Pinto R A, Weber W J, Zhang L, Huang Q, Landrum P F. Effects of polyethyleneimine-mediated functionalization of multi-walled carbon nanotubes on earthworm bioaccumulation and sorption by soils. Environ Sci Technol 2011; 45: 3718-24.

[51] Plata D L, Reddy C M, Gschwend P M. Thermogravimetry-mass spectrometry for carbon nanotube detection in complex mixtures. Environ Sci Technol 2012.

[52] Quispe D, Pérez-López R, Silva L F O, Nieto J M. Changes in mobility of hazardous elements during coal combustion in Santa Catarina power plant (Brazil). Fuel 2012; 94:495-503.

[53] Ribeiro J, Flores D, Ward C W, Silva L F O. Identification of nanominerals and nanoparticles in burning coal waste piles from Portugal. Sci Total Environ 2010; 408:6032-604.

[54] Shieh Y T, Yu T Y, Wang T L, Yang C H, Liao W T. Effects of pH on electrocatalytic activity of functionalized carbon nanotubes. Colloid Polym Sci 2012; 290:1-9.

[55] Shim H C, Song J W, Kwak Y K, Kim S, Han C S. Preferential elimination of metallic single-walled carbon nanotubes using microwave irradiation. Nanotechnology 2009; 20.

[56] Silva L F O, Oliveira M L S, Neace E R, O'Keefe K M K, Henke K R, Hower J C. Nanominerals and ultrafine particles in sublimates from the Ruth Mullins coal fire, Perry County, Eastern Kentucky, USA. Int J Coal Geol 2011a; 85:237-45.

[57] Silva L F O, Querol X, da Boit K M, Fdez-Ortiz de Vallejuelo S, Madariaga J M. Brazilian coal mining residues and sulphide oxidation by Fenton s reaction: an accelerated weathering procedure to evaluate possible environmental impact. J Hazard Mater 2011b; 186:516-25.

[58] Silva L F O, Oliveira M L S, Philippi V, Serra C, Dai S, Xue W, et al. Geochemistry of carbon nanotube assemblages in coal fire soot, Ruth Mullins fire, Perry County, Kentucky. Int J Coal Geol 2012a; 94:206-13.
[59] Silva L F O, Sampaio C H, Guedes A, Fdez-Ortiz de Vallejuelo S, Madar J M. Multianalytical approaches to the characterisation of minerals associated with coals and the diagnosis of their potential risk by using combined instrumental microspectroscopic techniques and thermodynamic speciation. Fuel 2012b; 94:52-63.
[60] Silva L F O, DaBoit K, Sampaio C H, Jasper A, Andrade M L, Kostova I J, et al. The occurrence of hazardous volatile elements and nanoparticles in Bulgarian coal fly ashes and the effect on human health exposure. Sci Total Environ 2012c; 416:513-26.
[61] Silva L F O, Jasper A, Andrade M L, Sampaio C H, Dai S, Li Xiao, et al. Applied investigation on the interaction of hazardous elements binding on ultrafine and nanoparticles in Chinese anthracite-derived fly ash. Sci Total Environ 2012d; 419:250-64.
[62] Sobek A, Bucheli T D. The behaviour and effects of nanoparticles in the E. Testing the resistance of single- and multi-walled carbon nanotubes to chemothermal oxidation used to isolate soots from environmental samples. Environ Pollut 2009; 157: 1065-71.
[63] Yang M, Kwon S, Kostov Y, Rasooly A, Rao G, Ghosh U. Study of the biouptake of labeled single-walled carbon nanotubes using fluorescence-based method. Environ Chem Lett 2011; 9:235-41.
[64] Zhao X, Liu R. Recent progress and perspectives on the toxicity of carbon nanotubes at organism, organ, cell, and biomacromolecule levels. Environ Int 2012; 40:244-55.

What is claimed is:

1. A method of detection of carbon nanotubes in a sample comprising the steps of:
providing a sample suspected of having one or more carbon nanotubes;
irradiating the sample with one or more microwave radiations;
adsorbing the one or more microwave radiations by the one or more carbon nanotubes;
generating one or more thermal emissions from the one or more carbon nanotubes;
detecting the one or more thermal emissions from the one or more carbon nanotubes in the sample; and
correlating the one or more thermal emissions to a nanotube concentration of one or more carbon nanotubes.

2. The method of claim 1, wherein the one or more microwave radiations comprises a first microwave radiation and a second microwave radiation.

3. The method of claim 1, wherein the first microwave radiation is 30 W at 2.45 GHz frequency and the second microwave radiation is 50 W at 2.45 GHz frequency.

4. The method of claim 1, wherein the one or more carbon nanotubes detection have a detection limit of <0.05 μg.

5. The method of claim 1, further comprising the step of comparing the one or more thermal emissions to a carbon nanotube temperature/concentration of standard.

6. The method of claim 1, further comprising the step of flowing a continuous flow of nitrogen directly onto the surface of the sample to prevent ignition.

7. The method of claim 1, wherein the sample comprises a biological sample or an environmental sample.

8. The method of claim 1, wherein the sample comprises a plant tissue, an animal tissue, a human tissue, a plant cell, an animal cell, a human cell, a cancer cell, and so forth.

9. The method of claim 1, wherein the sample comprises a plant root or an earthworm.

10. The method of claim 1, wherein the one or more carbon nanotubes comprise one or more single walled carbon nanotubes, one or more multi-walled nanotubes, or a combination thereof.

11. The method of claim 1, wherein the one or more microwave radiations is between 0-140 W, 5-130 W, 5-120 W, 5-110 W, 5-100 W, 10-90 W, 10-80 W, 20-70 W, 30-60 W, 30-50 W, 40-60 W, 40-50 W or incremental variations thereof.

12. The method of claim 1, wherein the one or more microwave radiations have a resolution of 0.1 W, 0.2 W, 0.3 W, 0.4 W, 0.5 W, 0.6 W, 0.7 W, 0.8 W, 0.9 W, 1 W, 1.1 W, 1.2 W, 1.3 W, 1.4 W, 1.5 W or more.

13. The method of claim 1, wherein the one or more microwave radiations have a frequency between 300 GHz-300 MHz or 1 mm-1 meter.

14. The method of claim 1, wherein the microwave radiation has a frequency of 2.45 GHz.

15. The method of claim 1, further comprising the step of contacting a thermocouple probe with the sample to measure a temperature change resulting from the one or more thermal emissions.

16. The method of claim 15, wherein the one or more thermal emissions is measured by a k-type beaded wire stainless steel thermocouple probe.

17. The method of claim 1, wherein the one or more carbon nanotubes comprise one or more single walled carbon nanotubes, one or more multi-walled carbon nanotubes, or a combination thereof.

18. The method of claim 17, wherein the one or more single walled carbon nanotubes have a diameter of between 0.1-2.0 nm, 0.2-1.9 nm, 0.3-1.8 nm, 0.4-1.8 nm, 0.5-1.7 nm, 0.6-1.6 nm, 0.7-1.5 nm, 0.7-1.3 nm or an incremental variation thereof.

19. The method of claim 17, wherein the one or more multi-walled carbon nanotubes have a diameter of 10-70 nm, 15-65 nm, 20-60 nm, 25-55 nm, 30-50 nm, 35-45 nm or an incremental variation thereof.

20. The method of claim 17, wherein the one or more multi-walled carbon nanotubes have a length of between 5-25 μm, 7-22 μm, 10-20 μm, or more than 25 μm.

* * * * *